US011972336B2

(12) United States Patent
Vaughan et al.

(10) Patent No.: US 11,972,336 B2
(45) Date of Patent: Apr. 30, 2024

(54) MACHINE LEARNING PLATFORM AND SYSTEM FOR DATA ANALYSIS

(71) Applicant: Cognoa, Inc., Palo Alto, CA (US)

(72) Inventors: Brent Vaughan, Portola Valley, CA (US); Abdelhalim Abbas, San Jose, CA (US); Dennis Wall, Palo Alto, CA (US)

(73) Assignee: Cognoa, Inc., Palo Alto, CA (US)

( * ) Notice: Subject to any disclaimer, the term of this patent is extended or adjusted under 35 U.S.C. 154(b) by 3 days.

(21) Appl. No.: 17/690,977

(22) Filed: Mar. 9, 2022

(65) Prior Publication Data

US 2023/0092866 A1   Mar. 23, 2023

Related U.S. Application Data

(63) Continuation-in-part of application No. 16/155,758, filed on Oct. 9, 2018, which is a continuation of application No. 16/010,284, filed on Jun. 15, 2018, now abandoned, which is a continuation of application No. PCT/US2016/067358, filed on Dec. 16, 2016.

(60) Provisional application No. 62/269,638, filed on Dec. 18, 2015.

(51) Int. Cl.
| | |
|---|---|
| *G06N 20/20* | (2019.01) |
| *A61B 5/00* | (2006.01) |
| *A61B 5/16* | (2006.01) |
| *G06F 18/214* | (2023.01) |
| *G06N 5/01* | (2023.01) |

(52) U.S. Cl.
CPC ............... *G06N 20/20* (2019.01); *A61B 5/16* (2013.01); *A61B 5/163* (2017.08); *A61B 5/168* (2013.01); *G06F 18/2148* (2023.01); *G06N 5/01* (2023.01); *A61B 5/0077* (2013.01); *A61B 2503/06* (2013.01)

(58) Field of Classification Search
CPC ..... A61B 2503/06; A61B 5/0077; A61B 5/16; A61B 5/168; A61B 5/163; G06N 5/003; G06N 20/20; G06K 9/6257
See application file for complete search history.

(56) References Cited

U.S. PATENT DOCUMENTS

| | | |
|---|---|---|
| 4,860,214 A | 8/1989 | Matsuda et al. |
| 5,722,418 A | 3/1998 | Bro |

(Continued)

FOREIGN PATENT DOCUMENTS

| | | |
|---|---|---|
| CA | 2857069 A1 | 5/2013 |
| CN | 101149767 A | 3/2008 |

(Continued)

OTHER PUBLICATIONS

Artoni et al., "Accessible education for autistic children: ABA-based didactic software", International Conference on Universal Access in Human-Computer Interaction (2011).

(Continued)

*Primary Examiner* — Rene T Towa
(74) *Attorney, Agent, or Firm* — Wilson Sonsini Goodrich & Rosati

(57) ABSTRACT

Disclosed herein is a machine learning platform and system for data analysis including for purposes of providing digital evaluations and therapeutics.

12 Claims, 18 Drawing Sheets

(56) References Cited

U.S. PATENT DOCUMENTS

| | | | |
|---|---|---|---|
| 5,807,114 A * | 9/1998 | Hodges | A61M 21/00 |
| | | | 434/30 |
| 6,186,145 B1 | 2/2001 | Brown | |
| 6,425,764 B1 * | 7/2002 | Lamson | G16H 30/40 |
| | | | 434/236 |
| 6,569,093 B2 | 5/2003 | Iliff | |
| 6,957,202 B2 | 10/2005 | Skaanning et al. | |
| 7,043,439 B2 | 5/2006 | Jost et al. | |
| 7,155,421 B1 | 12/2006 | Haldar | |
| 7,311,666 B2 | 12/2007 | Stupp et al. | |
| 7,958,066 B2 | 6/2011 | Pinckney et al. | |
| 7,974,872 B2 | 7/2011 | Katayama et al. | |
| 8,024,332 B2 | 9/2011 | Cao et al. | |
| 8,655,817 B2 | 2/2014 | De et al. | |
| 8,834,174 B2 | 9/2014 | Malik | |
| 9,305,059 B1 | 4/2016 | Glickman et al. | |
| 9,443,199 B2 | 9/2016 | Pinckney et al. | |
| 9,443,205 B2 | 9/2016 | Wall | |
| 10,052,057 B2 * | 8/2018 | Klin | A61B 5/16 |
| 10,311,645 B1 | 6/2019 | Ravindran et al. | |
| 10,478,112 B2 | 11/2019 | Wall | |
| 10,687,751 B2 | 6/2020 | Wall | |
| 10,839,950 B2 | 11/2020 | Vaughan | |
| 10,874,355 B2 | 12/2020 | Vaughan et al. | |
| 10,984,899 B2 | 4/2021 | Vaughan | |
| 11,024,422 B2 | 6/2021 | Wall | |
| 11,176,444 B2 | 11/2021 | Wall et al. | |
| 2001/0034615 A1 | 10/2001 | Wilkinson et al. | |
| 2001/0036444 A1 | 11/2001 | Placke et al. | |
| 2002/0002325 A1 | 1/2002 | Iliff | |
| 2002/0019747 A1 | 2/2002 | Ware et al. | |
| 2002/0035486 A1 | 3/2002 | Huyn et al. | |
| 2002/0042786 A1 | 4/2002 | Scarborough et al. | |
| 2003/0032069 A1 | 2/2003 | Muraca | |
| 2003/0191680 A1 | 10/2003 | Dewar | |
| 2004/0015337 A1 | 1/2004 | Thomas et al. | |
| 2004/0103001 A1 | 5/2004 | Mazar et al. | |
| 2004/0147840 A1 | 7/2004 | Duggirala et al. | |
| 2004/0197750 A1 | 10/2004 | Donaher et al. | |
| 2004/0210159 A1 * | 10/2004 | Kibar | A61B 5/165 |
| | | | 128/898 |
| 2004/0265784 A1 | 12/2004 | Stout | |
| 2005/0075887 A1 | 4/2005 | Bernard et al. | |
| 2005/0142524 A1 | 6/2005 | Simon et al. | |
| 2005/0176057 A1 | 8/2005 | Bremer et al. | |
| 2005/0187802 A1 | 8/2005 | Koeppel | |
| 2005/0197988 A1 | 9/2005 | Bublitz | |
| 2005/0209785 A1 | 9/2005 | Wells et al. | |
| 2005/0216243 A1 | 9/2005 | Graham et al. | |
| 2005/0260549 A1 | 11/2005 | Feierstein et al. | |
| 2006/0009683 A1 | 1/2006 | Sakai et al. | |
| 2006/0059145 A1 | 3/2006 | Henschke et al. | |
| 2006/0078856 A1 | 4/2006 | Kellman | |
| 2006/0282306 A1 | 12/2006 | Thissen-Roe | |
| 2007/0118399 A1 | 5/2007 | Avinash et al. | |
| 2007/0207449 A1 | 9/2007 | Feierstein | |
| 2008/0014566 A1 | 1/2008 | Chapman et al. | |
| 2008/0016024 A1 | 1/2008 | Andoh et al. | |
| 2009/0007924 A1 | 1/2009 | Iliff | |
| 2009/0016559 A1 | 1/2009 | Cleary | |
| 2009/0016599 A1 | 1/2009 | Eaton et al. | |
| 2009/0083075 A1 | 3/2009 | Henschke et al. | |
| 2009/0124886 A1 | 5/2009 | Wang et al. | |
| 2009/0137923 A1 | 5/2009 | Suffin et al. | |
| 2009/0182578 A1 | 7/2009 | Ozersky | |
| 2009/0259494 A1 | 10/2009 | Feder et al. | |
| 2010/0023346 A1 | 1/2010 | Paty et al. | |
| 2010/0068687 A1 | 3/2010 | Bertelsen | |
| 2010/0177950 A1 | 7/2010 | Donovan et al. | |
| 2010/0179928 A1 | 7/2010 | Hodgin | |
| 2010/0184093 A1 | 7/2010 | Donovan et al. | |
| 2010/0189818 A1 | 7/2010 | Tsai | |
| 2010/0280760 A1 | 11/2010 | Pi et al. | |
| 2010/0332430 A1 | 12/2010 | Caraviello et al. | |
| 2011/0082712 A1 | 4/2011 | Eberhardt, III et al. | |
| 2011/0119212 A1 | 5/2011 | De Bruin et al. | |
| 2011/0145161 A1 | 6/2011 | Scarborough et al. | |
| 2011/0184379 A1 | 7/2011 | Van Antwerp et al. | |
| 2011/0218253 A1 | 9/2011 | Lange et al. | |
| 2012/0004925 A1 | 1/2012 | Braverman et al. | |
| 2012/0028816 A1 | 2/2012 | Warren et al. | |
| 2012/0059282 A1 | 3/2012 | Agichtein et al. | |
| 2012/0101852 A1 | 4/2012 | Albert | |
| 2012/0102405 A1 | 4/2012 | Zuckerman et al. | |
| 2012/0108909 A1 | 5/2012 | Slobounov et al. | |
| 2012/0270199 A1 | 10/2012 | Malik | |
| 2013/0159010 A1 | 6/2013 | Paty et al. | |
| 2013/0178731 A1 | 7/2013 | Bosl | |
| 2013/0184603 A1 | 7/2013 | Rothman | |
| 2013/0184792 A1 | 7/2013 | Simon et al. | |
| 2013/0262357 A1 | 10/2013 | Amarasingham et al. | |
| 2013/0267441 A1 | 10/2013 | Momeni et al. | |
| 2014/0006319 A1 | 1/2014 | Anand et al. | |
| 2014/0024553 A1 | 1/2014 | Michalek et al. | |
| 2014/0052474 A1 | 2/2014 | Madan et al. | |
| 2014/0063236 A1 | 3/2014 | Shreve et al. | |
| 2014/0074848 A1 | 3/2014 | Kettunen et al. | |
| 2014/0092006 A1 * | 4/2014 | Boelter | G09G 5/363 |
| | | | 345/156 |
| 2014/0122109 A1 | 5/2014 | Ghanbari et al. | |
| 2014/0141983 A1 | 5/2014 | Singh et al. | |
| 2014/0148728 A1 * | 5/2014 | Eizenman | A61B 5/165 |
| | | | 600/558 |
| 2014/0219986 A1 | 8/2014 | Greene et al. | |
| 2014/0223462 A1 * | 8/2014 | Aimone | G16H 40/67 |
| | | | 725/10 |
| 2014/0253876 A1 * | 9/2014 | Klin | G16H 20/70 |
| | | | 351/210 |
| 2014/0279746 A1 | 9/2014 | De et al. | |
| 2014/0304200 A1 * | 10/2014 | Wall | G16H 10/20 |
| | | | 706/12 |
| 2014/0330576 A1 | 11/2014 | Bauer | |
| 2014/0336539 A1 * | 11/2014 | Torres | A61B 5/162 |
| | | | 600/595 |
| 2014/0342321 A1 * | 11/2014 | Wendt | G09B 7/06 |
| | | | 434/156 |
| 2014/0343450 A1 * | 11/2014 | Stack | A61B 5/4833 |
| | | | 600/300 |
| 2015/0004588 A1 | 1/2015 | Vats et al. | |
| 2015/0006192 A1 | 1/2015 | Sudharsan et al. | |
| 2015/0080671 A1 | 3/2015 | Christensen et al. | |
| 2015/0099946 A1 | 4/2015 | Sahin | |
| 2015/0119437 A1 | 4/2015 | Clark et al. | |
| 2015/0154372 A1 | 6/2015 | Soenksen et al. | |
| 2015/0197543 A1 | 7/2015 | Glass et al. | |
| 2015/0315182 A1 | 11/2015 | Lee et al. | |
| 2016/0022137 A1 * | 1/2016 | Wetzel | A61B 5/4076 |
| | | | 600/558 |
| 2016/0046990 A1 | 2/2016 | Hensel | |
| 2016/0135706 A1 | 5/2016 | Sullivan et al. | |
| 2016/0140859 A1 | 5/2016 | Jiao et al. | |
| 2016/0180038 A1 | 6/2016 | Clark et al. | |
| 2016/0180248 A1 | 6/2016 | Regan | |
| 2016/0203280 A1 | 7/2016 | Neville | |
| 2016/0209428 A1 | 7/2016 | Naviaux et al. | |
| 2016/0232328 A1 | 8/2016 | Sklar et al. | |
| 2016/0342756 A1 | 11/2016 | Wall | |
| 2016/0355924 A1 | 12/2016 | Jenkins | |
| 2017/0035792 A1 | 2/2017 | Montagnier et al. | |
| 2017/0069216 A1 | 3/2017 | Vaughan et al. | |
| 2017/0091423 A1 | 3/2017 | Kumar et al. | |
| 2017/0160878 A1 | 6/2017 | Endo et al. | |
| 2017/0169178 A1 * | 6/2017 | Beehler | G16H 50/30 |
| 2017/0188930 A1 * | 7/2017 | Lahvis | A61B 5/168 |
| 2017/0262609 A1 | 9/2017 | Perlroth et al. | |
| 2017/0365101 A1 * | 12/2017 | Samec | G16H 50/20 |
| 2018/0098724 A1 | 4/2018 | Lu et al. | |
| 2018/0132780 A1 * | 5/2018 | Saar | A61B 5/0077 |
| 2018/0184964 A1 | 7/2018 | Simon et al. | |
| 2018/0366144 A1 | 12/2018 | Ashoori et al. | |
| 2019/0019581 A1 * | 1/2019 | Vaughan | G16H 50/20 |
| 2019/0038202 A1 | 2/2019 | Wall | |
| 2019/0043610 A1 | 2/2019 | Vaughan | |

(56) References Cited

U.S. PATENT DOCUMENTS

| | | | |
|---|---|---|---|
| 2019/0043618 | A1 | 2/2019 | Vaughan et al. |
| 2019/0043619 | A1 | 2/2019 | Vaughan et al. |
| 2019/0088366 | A1 | 3/2019 | Vaughan et al. |
| 2019/0244127 | A1 | 8/2019 | Amado et al. |
| 2021/0068766 | A1 | 3/2021 | Vaughan et al. |
| 2021/0133509 | A1 | 5/2021 | Wall et al. |
| 2021/0174919 | A1 | 6/2021 | Vaughan |
| 2021/0335489 | A1 | 10/2021 | Wall |
| 2022/0157466 | A1 | 5/2022 | Vaughan et al. |
| 2022/0369976 | A1 | 11/2022 | Abbas et al. |

FOREIGN PATENT DOCUMENTS

| | | | | |
|---|---|---|---|---|
| CN | 101421736 | A | 4/2009 | |
| CN | 101499078 | A | 8/2009 | |
| CN | 101821741 | A | 9/2010 | |
| CN | 102265279 | A | 11/2011 | |
| CN | 102663129 | A | 9/2012 | |
| CN | 102971755 | A | 3/2013 | |
| CN | 103473631 | A | 12/2013 | |
| CN | 103493054 | A | 1/2014 | |
| CN | 103714261 | A | 4/2014 | |
| CN | 104504297 | A | 4/2015 | |
| CN | 104902806 | A | 9/2015 | |
| EP | 0424869 | | 2/1991 | |
| EP | 3941340 | A1 | 1/2022 | |
| JP | 2001034688 | A | 2/2001 | |
| JP | 2002318858 | A | 10/2002 | |
| JP | 2007249878 | A | 9/2007 | |
| JP | 2011255106 | A | 12/2011 | |
| JP | 2015228202 | A | 12/2015 | |
| JP | 2017504087 | A | 2/2017 | |
| WO | WO-9521419 | A1 | 8/1995 | |
| WO | WO-9705553 | A1 | 2/1997 | |
| WO | WO-2008124138 | A1 | 10/2008 | |
| WO | WO-2010059709 | A2 | 5/2010 | |
| WO | WO-2012082056 | A1 | 6/2012 | |
| WO | WO-2013062937 | A2 | 5/2013 | |
| WO | WO-2014127065 | A2 | 8/2014 | |
| WO | WO-2014164858 | A1 | 10/2014 | |
| WO | WO-2015006364 | A2 | 1/2015 | |
| WO | WO-2015066203 | A2 | 5/2015 | |
| WO | WO-2016110804 | A1 * | 7/2016 | ............... A61B 3/16 |
| WO | WO-2017027709 | A1 | 2/2017 | |
| WO | WO-2017106770 | A1 | 6/2017 | |
| WO | WO-2018090009 | A1 | 5/2018 | |
| WO | WO-2020198065 | A1 | 10/2020 | |
| WO | WO-2021046412 | A1 | 3/2021 | |

OTHER PUBLICATIONS

Atherton, G., et al., "Autism through the ages: a mixed methods approach to understanding how age and age of diagnosis affect quality of life", J Autism Dev Disord, doi: 10.1007/s10803-021-05235-x.
Bailey, et al. Autism as a strongly genetic disorder: evidence from a British twin study. Psychol Med. Jan. 1995;25(1):63-77.
Bernier, et al. Psychopathology, families, and culture: autism. Child Adolesc Psychiatr Clin N Am. Oct. 2010;19(4):855-67.
Berument, et al. Autism screening questionnaire: diagnostic validity. Br J Psychiatry. Nov. 1999; 175:444-51.
Breiman et al.: Chapter 6 Medical diagnosis and prognosis. Classification and regression trees. Chappman & Hall/CRC (1984) (pp. 174-346).
Breiman. Random Forests. Machine Learning 45:5-32 (2001).
Brewer et al., Pinteresce: Exploring Reminiscence as an Incentive to Digital Reciprocity for Older Adults. CSCW'15 Companion (2015).
Cicchetti, et al. Reliability of the ADI-R: multiple examiners evaluate a single case. J Autism Dev Disord. Apr. 2008;38(4):764-70. Epub Dec. 5, 2007.

Cohen. Fast effective rule induction. Proceedings of the Twelfth International Conference on Machine Learning. (pp. 115-123) (1995).
Duda, et al. Clinical Evaluation of a Novel and Mobile Autism Risk Assessment. J Autism Dev Disord. Jun. 2016;46(6):1953-61. .
Duda, et al. Testing the accuracy of an observation-based classifier for rapid detection of autism risk Transl Psychiatry. Aug. 12, 2014;4:e424.
Duda, et al. Testing the accuracy of an observation-based classifier for rapid detection of autism risk. Transl Psychiatry. Apr. 28, 2015;5:e556. (Addendum).
Duda et al., Use of Machine Learning for Behavioral Distinction of Autism and ADHD. Transl Psychiatry 6(2):e732 (2016).
Elder et al., Clinical impact of early diagnosis of autism on the prognosis and parent-child relationships. Psychology Research and Behavior Management 10: 283-292 (2017).
Fischbach, et al. The Simons Simplex Collection: a resource for identification of autism genetic risk factors. Neuron. Oct. 21, 2010;68(2):192-5.
Fisher et al., DISC Interviewer Manual. Section 2 Computerized Versions of the DISC (2006).
Frank, et al. A simple approach to ordinal prediction. European conference on Maching Learning; Freiburg, Germany, Springer-Verlag 2001:145-156.
Frank, et al. Data mining in bioinformatics using Weka. Bioinformatics. Oct. 12, 2004;20(15):2479-81. Epub Apr. 8, 2004.
Frank et al. Generating accurate rule sets without global optimization. In: Machine Learning: Proceedings of the Fifteenth International Conference: 1998; San Francisco, CA, Morgan Kaufmann Publishers (8 pgs).
Freund, et al. A decision-theoretic generalization of on-line learning and an application to boosting. Journal of computer and system sciences 55.1 (1997): 119-139.
Freund, et al. Experiments with a new boosting algorithm. In: Proceedings of the International Conference on Machine Learning: 1996, San Francisco, Morgan Kautinann: pp. 148-156.
Freund, et al. The alternating decision tree learning algorithm. In: Machine Learning: Proceedings of the Sixteenth International Conference. 1999, pp. 124-133.
Fusaro, et al. The potential of accelerating early detection of autism through content analysis of YouTube videos. PLoS One. Apr. 16, 2014;9(4):e93533.
Gaines, et al. Induction of ripple-down rules applied to modeling large databases. Journal of Intelligent Information Systems 5.3 (1995): 211-228.
Gama. Functional trees. Machine Learning 55:219-250 (2004).
Geschwind et al. The autism genetic resource exchange: a resource for the study of autism and related neuropsychiatric conditions. The American Journal of Human Genetics 69:463-466 (2001).
Gillberg et al. Early detection of autism. Diagnostic instruments for clinicians. European Child & Adolescent Psychiatry 5.2:67-74. (1996).
Golarai, G. et al. "Autism and the development of face processing", Clinical Neuroscience Research, 2006, vol. 6 , No. 3, pp. 145-106.
Gotham, et al. The Autism Diagnostic Observation Schedule: revised algorithms for improved diagnostic validity. J Autism Dev Disord. Apr. 2007;37(4):613-27. Epub Dec. 16, 2006.
Gura, et al. Autism spectrum disorder screening in primary care. J Dev Behav Pediatr. Jan. 2011;32(1):48-51.
Hall et al. The WEKA data mining software: an update. SIGKDD Explorations Newsletter 11:10-18 (2009).
Hamidpour, et al., Antipurinergic therapy with Suramin as a treatment for autism spectrum disorder, Journal of Biomedical sciences, Mar. 29, 2016; 5:pp. 17; abstract, p. 1, p. 2, p. 4, p. 5.
Hirsch, S. et al. Development of a questionnaire weighted scoring system to target diagnostic examinations for asthma in adults: a modelling study. BMC Fam. Pract. 5:30 pp. 1-13 (2004) [E-pub Dec. 17, 2004].
Holmes et al. Multiclass alternating decision trees. Machine learning: ECML 2002. Springer Berlin Heidelberg, (pp. 161-172) (2002).
Holte. Very simple classification rules perform well on most commonly used datasets. Machine learning 11:63-91 (1993).
Howlin. Chapter 3—Identifying and assessing children with autism or asperger syndrome. Children with Autism and Asperger's Syn-

(56) References Cited

OTHER PUBLICATIONS drome: A Guide for Practitioners and Carers. UK: John Wiley and Sons (1998) (pp. 52-75, 294-321).
Kobak et al. Web-based training in early autism screening: results from a pilot study. Telemed J E Health. Oct. 2011; 17(8):640-4.
Kohavi. A study of cross-validation and bootstrap for accuracy estimation and model selection. In: Proceedings IJCAI-95: 1995: Montreal, Morgan Kaufmann, Los Altos, CA: 1137-1143.
Kosmicki, et al. Searching for a minimal set of behaviors for autism detection through feature selection-based machine learning. Transl Psychiatry. Feb. 24, 2015;5:e514.
Landwehr et al. Logistic model trees. Machine Learning 59:161-205 (2005).
Lee et al., How to Create Suitable Augmented Reality Application to Teach Social Skills for Children with ASD. IntechOpen 76476: 119-138 (2018).
Lord et al. Autism Diagnostic Interview—Revised: A revised version of a diagnostic interview for caregivers of individuals with possible pervasive developmental disorders. J Autism Dev Discord 24(5):659-685 (1994).
Lord, et al. Autism diagnostic observation schedule: a standardized observation of communicative and social behavior. J Autism Dev Disord. Jun. 1989; 19(2):185-212.
Lord et al. The Autism Diagnostic Observation Schedule—Generic: A Standard Measure of Social and Communication Deficits Associated with the Spectrum of Autism. J Autism Dev Discord 30(3):205-223 (2000).
Martin. Instance-Based learning: Nearest neighbor with generalization. Hamilton, New Zealand, University of Waikato (83 pgs) (1995).
Mayes et al., Autism and ADHD: Overlapping and discriminating symptoms. Research in Autism Spectrum Disorders 6(1) :277-285 (2012).
Moore et al. Cached Sufficient Statistics for Efficient Machine Learning with Large Datasets. JAIR 8:67-91 (1998).
Moyer, M.W., "Gut Bacteria May Play a Role in Autism", Scientific American, Sep. 1, 2014, pp. 1-4.
Muangnak et al. Classification students with learning disabilities using naive bayes classifier and decision tree. The 6th International Conference on Networked Computing and Advanced Information Management. IEEE, 2010.
Ogden, et al., Suramin as a chemosensitizer: Oral pharmacokinetics in rats, Pharmaceutical research, Nov. 2004;21:2058-2063; p. 2058.
Ordonez, C. et al. Machine learning techniques applied to the determination of osteoporosis incidence in post-menopausal women. Mathematical and Computer Modelling, 50:673-679 (2009).
PCT/US2012/061422 International Search Report and Written Opinion dated May 24, 2013.
PCT/US2016/046557 International Search Report and Written Opinion dated Nov. 3, 2016.
PCT/US2016/067358 International Search Report and Written Opinion dated Apr. 13, 2017.
PCT/US2020/049492 International Search Report and Written Opinion dated Dec. 10, 2020.
Pinto-Martin, et al. Screening strategies for autism spectrum disorders in pediatric primary care. J Dev Behav Pediatr. Oct. 2008;29(5):345-50.
Pisula, E. Parents of children with autism: review of current research. Arch Psychiatry Psychother, 2003, 5: 51-63.
Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, The Netherlands, Jul. 16, 2015; http://ceur-ws.org/Vol-1565/ (Year: 2015).
Planjner, Slide presentation on Bayesian Network Models for Adaptive Testing: Proceeding of the Twelfth Bayesian Modeling Applications Workshop (2015).
Quinlan. C4. 5: Programming for machine learning. Morgan Kaufmann (6 pgs) (1993).
Risi, et al. Combining information from multiple sources in the diagnosis of autism spectrum disorders. Journal of the American Academy of Child & Adolescent Psychiatry, 2006, 45(9): 1094-1103.
Robins, et al. The Modified Checklist for Autism in Toddlers: an initial study investigating the early detection of autism and pervasive developmental disorders. J Autism Dev Disord. Apr. 2001;31(2):131-44.
Rosipal et al.: Overview and Recent Advances in Partial Least Squares. Lecture Notes in Computer Science book series(LNTCS). 3940:34-51 doi:10.1007/11752790_2 (2005).
Rutter et al. Autism diagnostic interview—revised. Los Angeles, CA: Western Psychological Services 29:30 (2003).
Santosh et al. The construction and validation of a short form of the developmental, diagnostic and dimensional interview. Eur Child Adolesc Psychiatry. Aug. 2009;18(8):521-4.
Shattuck, et al. Timing of identification among children with an autism spectrum disorder: findings from a population-based surveillance study. J Am Acad Child Adolesc Psychiatry. May 2009;48(5):474-83.
Shi. Best-first decision tree learning. Master Thesis, The University of Waikato (120 pgs) (2007).
Skuse et al. The developmental, dimensional and diagnostic interview (3di): a novel computerized assessment for autism spectrum disorders. Journal of the American Academy of Child & Adolescent Psychiatry 43.5:548-558 (2004).
Sok et al.: Multivariate alternating decision trees, Pattern Recognition, 50:195-209 doi:10.1016/j.patcog.2015.08.014 (2016).
Tadevosyan-Leyfer, et al. A principal components analysis of the Autism Diagnostic Interview—Revised. J Am Acad Child Adolesc Psychiatry. Jul. 2003;42(7):864-72.
Van Stralen et al. Diagnostic methods I: sensitivity, specificity, and other measures of accuracy. Kidney Int. 75(12):1257-1263 (2009).
Wall et al. Use of artificial intelligence to shorten the behavioral diagnosis of autism. PLoS One. 2012;7(8):e43855.
Wall, et al. Use of machine learning to shorten observation-based screening and diagnosis of autism. Transl Psychiatry. Apr. 10, 2012;2:e100.
Ward et al., The Autistic Behavioural Indicators Instrument (ABII): Development and instrument utility in discriminating autistic disorder from speech and language impairment and typical development, Research in Autism Spectrum Disorders 4.1 (2010): 28-42.
Wenner, M. Gut Bacteria May Play a Role in Autism. Scientific American, pp. 1-4, Sep. 1, 2014.
Wiggins, et al. Examination of the time between first evaluation and first autism spectrum diagnosis in a population-based sample. J Dev Behav Pediatr. Apr. 2006;27(2 Suppl):S79-87.
Witten et al. Data Mining: Practical Machine Learning Tools and Techniques with Java Implementations. Morgan Kaufmann, Amsterdam, Second Edition (558 pgs) (Oct. 2005).
Witten et al., Weka: Practical Machine Learning Tools and Techniques with Java Implementations, University of Waikato, Department of Computer Science, 1999. (4pp).
Sasagawa, Karen et al. A trial evaluation of communication abilities using a log versatile communication aid VCAN/3A. The Institue of Electronics. vol. 114, No. 512 (2015): 119-124.
Spencer et al. Attention-deficit/hyperactivity disorder and comorbidity. Pediatr Clin North Am. 46(5):915-927, vii. doi: 10.1016/s0031-3955(05)70163-2 (1999).
U.S. Appl. No. 16/155,758 Office Action dated Sep. 21, 2023.
U.S. Appl. No. 17/591,190 Office Action dated May 12, 2023.

* cited by examiner

MACHINE LEARNING PLATFORM AND SYSTEM FOR DATA ANALYSIS

CROSS-REFERENCE

This application is a continuation-in-part of U.S. patent application Ser. No. 16/155,758, filed Oct. 9, 2018, which is a continuation of U.S. patent application Ser. No. 16/010,284, filed Jun. 15, 2018, which is a continuation of International Patent Application No. PCT/US2016/067358, filed Dec. 16, 2016, which claims priority to U.S. Provisional Patent Application No. 62/269,638, filed Dec. 18, 2015, the entire contents of which are herein incorporated by reference for all purposes.

BACKGROUND OF THE INVENTION

Prior methods and apparatus for digital diagnosis and treatment of patients are less than ideal in at least some respects. Although digital data can be acquired from patients in many ways, the integration of this digital data with patient treatment is less than ideal. For example, merely recording activity of a patient and suggesting an activity according to a predetermined treatment plan may not provide the best treatment for the patient.

Although digital diagnosis with machine learning has been proposed, the integration of digital diagnostics with patient treatments can be less than ideal. For example, classifiers used to diagnose patients may be less than ideally suited to most effectively align treatments with diagnoses or monitor treatments.

Prior methods and apparatus for diagnosing and treating cognitive function of people such as people with a developmental disorder can be less than ideal in at least some respects. Unfortunately, a less than ideal amount of time, energy and money can be required to obtain a diagnosis and treatment, and to determine whether a subject is at risk for decreased cognitive function such as, dementia, Alzheimer's or a developmental disorder. Examples of cognitive and developmental disorders less than ideally treated by the prior approaches include autism, autistic spectrum, attention deficit disorder, attention deficit hyperactive disorder and speech and learning disability, for example. Examples of mood and mental illness disorders less than ideally treated by the prior approaches include depression, anxiety, ADHD, obsessive compulsive disorder, and substance disorders such as substance abuse and eating disorders. The prior approaches to diagnosis and treatment of several neurodegenerative diseases can be less than ideal in many instances, and examples of such neurodegenerative diseases include age related cognitive decline, cognitive impairment, Alzheimer's disease, Parkinson's disease, Huntington's disease, and amyotrophic lateral sclerosis ("ALS"), for example. The healthcare system is under increasing pressure to deliver care at lower costs, and prior methods and apparatus for clinically diagnosing or identifying a subject as at risk of a developmental disorder can result in greater expense and burden on the health care system than would be ideal. Further, at least some subjects are not treated as soon as ideally would occur, such that the burden on the healthcare system is increased with the additional care required for these subjects.

The identification and treatment of cognitive disorders in subjects can present a daunting technical problem in terms of both accuracy and efficiency. Many prior methods for identifying and treating such disorders are often time-consuming and resource-intensive, requiring a subject to answer a large number of questions or undergo extensive observation under the administration of qualified clinicians, who may be limited in number and availability depending on the subject's geographical location. In addition, many prior methods for identifying and treating behavioral, neurological or mental health disorders have less than ideal accuracy and consistency, as subjects to be evaluated using such methods often present a vast range of variation that can be difficult to capture and classify. A technical solution to such a technical problem would be desirable, wherein the technical solution can improve both the accuracy and efficiency for diagnosis and treatment. Ideally, such a technical solution would reduce the required time and resources for administering a method for identifying and treating attributes of cognitive function, such as behavioral, neurological or mental health disorders, and improve the accuracy and consistency of the identification outcomes of subjects.

Furthermore, although prior lengthy tests with questions can be administered to caretakers such as parents in order to diagnose or identify a subject as at risk for a developmental disorder, such tests can be quite long and burdensome. For example at least some of these tests have over one hundred questions, and more than one such lengthy test may be administered further increasing the burden on health care providers and caretakers. Additional data may be required such as clinical observation of the subject, and clinical visits may further increase the amount of time and burden on the healthcare system. Consequently, the time between a subject being identified as needing to be evaluated and being clinically identified as at risk or diagnosed with a developmental delay can be several months, and in some instances over a year.

Also, it would be helpful if diagnostic methods and treatments could be applied to subjects to advance cognitive function for subjects with advanced, normal and decreased cognitive function.

In light of the above, improved digital therapeutics for patients are needed. Ideally, such digital therapeutics would provide a customized treatment plan for a patient, receive updated diagnostic data in response to the customized treatment plan to determine progress, and update the treatment plan accordingly. There is also a need for improved methods and apparatus of diagnosing, treating and identifying subjects who are at risk. Ideally such methods and apparatus would monitor patients with fewer questions, decreased amounts of time, and provide clinically acceptable sensitivity and specificity in a clinical or nonclinical environment, which can be used to monitor and adapt treatment efficacy. Ideally, such methods and apparatus can also be used to determine the developmental progress of a subject, and offer treatment to advance developmental progress.

SUMMARY OF THE INVENTION

The digital personalized medicine systems and methods described herein provide digital diagnostics and digital therapeutics to patients. The digital personalized medicine system uses digital data to assess or diagnose symptoms of a patient in ways that inform personalized or more appropriate therapeutic interventions and improved diagnoses.

In one aspect, the digital personalized medicine system comprises digital devices with processors and associated software configured to: use data to assess and diagnose a patient; capture interaction and feedback data that identify relative levels of efficacy, compliance and response resulting from the therapeutic interventions; and perform data analysis, including at least one of machine learning, artificial intelligence, and statistical models to assess user data and user profiles to further personalize, improve or assess efficacy of the therapeutic interventions.

In some instances, the system is configured to use digital diagnostics and digital therapeutics. Digital diagnostics and digital therapeutics can comprise a system or methods for digitally collecting information and processing and analyzing the provided data to improve the medical, psychological, or physiological state of an individual. A digital therapeutic system can apply software based learning to analyze user data, monitor and improve the diagnoses and therapeutic interventions provided by the system.

Digital diagnostics data in the system can comprise data and meta-data collected from the patient, or a caregiver, or a party that is independent of the individual being assessed. In some instances the collected data can comprise monitoring behaviors, observations, judgements, or assessments may be made by a party other than the individual. In further instances the assessment can comprise an adult performing an assessment or provide data for an assessment of a child or juvenile. The data and meta-data can be either actively or passively in digital format via one or more digital devices such as mobile phones, video capture, audio capture, activity monitors, or wearable digital monitors.

The digital diagnostic uses the data collected by the system about the patient, which may include complimentary diagnostic data captured outside the digital diagnostic, with analysis from tools such as machine learning, artificial intelligence, and statistical modeling to assess or diagnose the patient's condition. The digital diagnostic can also provide assessment of a patient's change in state or performance, directly or indirectly via data and meta-data that can be analyzed by tools such as machine learning, artificial intelligence, and statistical modeling to provide feedback into the system to improve or refine the diagnoses and potential therapeutic interventions.

Data assessment and machine learning from the digital diagnostic and corresponding responses, or lack thereof, from the therapeutic interventions can lead to the identification of novel diagnoses for patients and novel therapeutic regimens for both patents and caregivers.

Types of data collected and utilized by the system can include patient and caregiver video, audio, responses to questions or activities, and active or passive data streams from user interaction with activities, games or software features of the system, for example. Such data can also include meta-data from patient or caregiver interaction with the system, for example, when performing recommended activities. Specific meta-data examples include data from a user's interaction with the system's device or mobile app that captures aspects of the user's behaviors, profile, activities, interactions with the software system, interactions with games, frequency of use, session time, options or features selected, and content and activity preferences. Data may also include data and meta-data from various third party devices such as activity monitors, games or interactive content.

Digital therapeutics can comprise instructions, feedback, activities or interactions provided to the patient or caregiver by the system. Examples include suggested behaviors, activities, games or interactive sessions with system software and/or third party devices.

In further aspects, the digital therapeutics methods and apparatus disclosed herein can diagnose and treat a subject as at risk of having one or more behavioral, neurological or mental health disorders among a plurality of behavioral, neurological or mental health disorders in a clinical or nonclinical setting, with fewer questions, in a decreased amounts of time, and with clinically acceptable sensitivity and specificity in a clinical environment, and provide treatment recommendations. This can be helpful when a subject initiates treatment based on an incorrect diagnosis, for example. A processor can be configured with instructions to identify a most predictive next question or most instructive next symptom or observation, such that a person can be diagnosed or identified as at risk and treated with fewer questions or observations. Identifying the most predictive next question or most instructive next symptom or observation in response to a plurality of answers has the advantage of increasing the sensitivity and the specificity and providing treatment with fewer questions. In some instances, an additional processor can be provided to predict or collect information on the next more relevant symptom. The methods and apparatus disclosed herein can be configured to evaluate and treat a subject for a plurality of related disorders using a single test, and diagnose or determine the subject as at risk of one or more of the plurality of disorders using the single test. Decreasing the number of questions presented or symptoms or measurements used can be particularly helpful where a subject presents with a plurality of possible disorders of which can be treated. Evaluating the subject for the plurality of possible disorders using just a single test can greatly reduce the length and cost of the evaluation procedure and improve treatment. The methods and apparatus disclosed herein can diagnose and treat subject at risk for having a single disorder among a plurality of possible disorders that may have overlapping symptoms.

While the most predictive next question, most instructive next symptom or observation used for the digital therapeutic treatment can be determined in many ways, in many instances the most predictive next question, symptom or observation is determined in response to a plurality of answers to preceding questions or observation that may comprise prior most predictive next question, symptom or observation to evaluate the treatment and provide a closed loop assessment of the subject. The most predictive next question, symptom or observation can be determined statistically, and a set of possible most predictive next questions, symptoms or observations can be evaluated to determine the most predictive next question, symptom or observation. In many instances, observations or answers to each of the possible most predictive next questions are related to the relevance of the question or observation, and the relevance of the question or observation can be determined in response to the combined feature importance of each possible answer to a question or observation. Once a treatment has been initiated, the questions, symptoms or can be repeated or different questions, symptoms or observations used to more accurately monitor progress and suggest changes to the digital treatment. The relevance of a next question, symptom or observation can also depend on the likely variance of the ultimate assessment among different answer choices of the question or potential options for an observation. For example, a question for which the answer choices might have a significan impact on the ultimate assessment down the line can be deemed more relevant than a question for which the answer choices might only help to discern differences in severity for one particular condition, or are otherwise less consequential.

Aspects of the present disclosure provide digital therapeutic systems to treat a subject with a personal therapeutic treatment plan. An exemplary system may comprise one or more processors comprising software instructions for a diagnostic module and a therapeutic module. The diagnostic module may receive data from the subject and output diagnostics data for the subject. The diagnostic module may comprise one or more of machine learning, a classifier, artificial intelligence, or statistical modeling based on a subject population to determine the diagnostic data for the subject. The therapeutic module may receive the diagnostic data and output the personal therapeutic treatment plan for the subject. The therapeutic module may comprise one or more of machine learning, a classifier, artificial intelligence, or statistical modeling based on at least a portion the subject population to determine and output the personal therapeutic treatment plan of the subject. The diagnostic module may be configured to received updated subject data from the subject in response to the therapy of the subject and generate updated diagnostic data from the subject. The therapeutic module may be configured to receive the updated diagnostic data and output an updated personal treatment plan for the subject in response to the diagnostic data and the updated diagnostic data.

In some embodiments, the diagnostic module comprises a diagnostic machine learning classifier trained on the subject population and the therapeutic module comprises a therapeutic machine learning classifier trained on the at least the portion of the subject population. The diagnostic module and the therapeutic module may be arranged for the diagnostic module to provide feedback to the therapeutic module based on performance of the treatment plan. The therapeutic classifier may comprise instructions trained on a data set comprising a population of which the subject is not a member. The subject may comprise a person who is not a member of the population.

In some embodiments, the diagnostic module comprises a diagnostic classifier trained on plurality of profiles of a subject population of at least 10,000 people and therapeutic profile trained on the plurality of profiles of the subject population.

Aspects of the present disclosure also provide digital personalized treatment systems. An exemplary system may comprise (i) software and digital devices that use data to assess and diagnose a subject, (ii) software and digital devices that capture interaction and feedback data that identify relative levels of efficacy, compliance, and response resulting from the therapeutic interventions, and (iii) data analysis, including machine learning, AI, and statistical models that assess user data and user profiles to further personalize, improve, or assess efficacy of the therapeutic interventions.

In some embodiments, the system comprises software based learning that allows the system to use its user data to monitor and improve its diagnoses and therapeutic interventions.

In some embodiments, digital diagnostics in the system comprises data and meta-data collected from the subject, or a caregiver, one or more of actively or passively in digital format via different digital devices such as mobile phones, video capture, audio capture, activity monitors, or wearable digital monitors.

In some embodiments, the digital diagnostic uses the data collected by the system about the subject, with or without complimentary diagnostic data captured outside the digital diagnostic, with analysis from tools such as machine learning, artificial intelligence and statistical modeling to assess or diagnose the subject's condition.

In some embodiments, the digital diagnostic further enables the assessment of a subject's change in state or performance, directly or indirectly via data and meta-data that can be analyzed by tools such as machine learning, artificial intelligence, and statistical modeling, to provide feedback into the system to improve or refine the diagnoses and potential therapeutic interventions.

In some embodiments, the data assessment and machine learning from the digital diagnostic and corresponding responses, or lack thereof, from the therapeutic interventions is configured to identify novel diagnoses for subjects and novel therapeutic regimens for both patents and caregivers.

In some embodiments, types of data collected and utilized by the system comprises subject and caregiver video, audio, responses to questions or activities and, active or passive data streams from user interaction with activities, games, or software features of the system.

In some embodiments, meta-data comprises data from a user's interaction with the system's device or mobile app that captures profiles of one or more of the user's behaviors, profile, activities, interactions with the software system, interactions with games, frequency of use, session time, options or features selected, content or activity preferences.

In some embodiments, data comprises data and meta-data from various third party devices such as activity monitors, games or interactive content.

In some embodiments, digital therapeutics comprises instructions, feedback, activities, or interactions provided to the subject or caregiver with a mobile device.

In some embodiments, the system comprises instructions to provide suggested behaviors, activities, games, or interactive sessions with system software and/or third party devices.

In some embodiments, the system comprises instructions to diagnose and treat one or more of cognitive or behavior development, neurodegenerative conditions, cognitive and behavioral disorders or conditions, including mood disorders.

Aspects of the present disclosure also provide systems to diagnose and treat a subject. An exemplary system may comprise a diagnostic module to receive subject data and output diagnostic data of the subject and a therapeutic module to receive the diagnostic data and output a therapeutic treatment for the subject, wherein the diagnostic module and the therapeutic module are arranged with a feedback loop to update the treatment in response to diagnostic data.

Aspects of the present disclosure also provide mobile devices to deliver digital personalized treatment. An exemplary mobile device may comprise a display and a processor configured with instructions to generate a user profile in response to user interactions with the device, receive and display therapeutic instructions to the user in response the user profile, update the user profile in response to treatment and transmit the updated user profile to a remote server, receive updated therapeutic instructions from the server, and display therapeutic updated instructions to the user.

Aspects of the present disclosure also provide digital therapeutic systems to treat a subject with a personal therapeutic treatment plan. An exemplary system may comprise a processor comprising instructions for a diagnostic module to receive data from the subject and output diagnostics data for the subject and a therapeutic module to receive the diagnostic data and output the personal therapeutic treatment plan for the subject. The personal therapeutic treatment plan may comprise digital therapeutics.

In some embodiments, the digital therapeutics comprises instructions, feedback, activities, or interactions provided to the subject or caregiver. The digital therapeutics may be provided with a mobile device.

In some embodiments, the diagnostics data and the personal therapeutic treatment plan are provided to a third-party system. The third-party system may comprise a computer system of a health care professional or a therapeutic delivery system.

In some embodiments, the diagnostic module is configured to receive updated subject data from the subject in response to a feedback data of the subject and generate updated diagnostic data. The therapeutic module may be configured to receive the updated diagnostic data and output an updated personal treatment plan for the subject in response to the diagnostic data and the updated diagnostic data. The updated subject data is received in response to a feedback data that identifies relative levels of efficacy, compliance, and response resulting from the personal therapeutic treatment plan.

In some embodiments, the diagnostic module comprises a machine learning, a classifier, artificial intelligence, or statistical modeling based on a subject population to determine the diagnostic data. The therapeutic module comprises a machine learning, a classifier, artificial intelligence, or statistical modeling based on at least a portion the subject population to determine the personal therapeutic treatment plan of the subject.

In some embodiments, the diagnostic module comprises a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features of the system.

In some embodiments, the subject has a risk selected from the group consisting of a behavioral disorder, neurological disorder and mental health disorder. The behavioral, neurological or mental health disorder may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

In some embodiments, the diagnostic module is configured for an adult to perform an assessment or provide data for an assessment of a child or juvenile.

In some embodiments, the diagnostic module is configured for a caregiver or family member to perform an assessment or provide data for an assessment of the subject.

Aspects of the present disclosure also provide methods of treating a subject with a personal therapeutic treatment plan. An exemplary method may comprise a diagnostic process of receiving data from the subject and outputting diagnostics data for the subject and a therapeutic process of receiving the diagnostic data and outputting the personal therapeutic treatment plan for the subject. The personal therapeutic treatment plan may comprise digital therapeutics.

In some embodiments, the digital therapeutics comprises instructions, feedback, activities or interactions provided to the subject or caregiver. The digital therapeutics may be provided with a mobile device.

In some embodiments, the method may further comprise a providing the diagnostics data and the personal therapeutic treatment plan to a third-party system. The third-party system may comprise a computer system of a health care professional or a therapeutic delivery system.

In some embodiments, diagnostic process further comprises receiving updated subject data from the subject in response to a feedback data of the subject and generating updated diagnostic data, and therapeutic process further comprises receiving the updated diagnostic data and outputting an updated personal treatment plan for the subject in response to the diagnostic data and the updated diagnostic data. The updated subject data may be received in response to a feedback data that identifies relative levels of efficacy, compliance, and response resulting from the personal therapeutic treatment plan.

In some embodiments, the diagnostic process is performed by a process selected from the group consisting of machine learning, a classifier, artificial intelligence, and statistical modeling based on a subject population to determine the diagnostic data. The therapeutic process may be performed by a process selected from the group consisting of machine learning, a classifier, artificial intelligence, or statistical modeling based on at least a portion the subject population to determine the personal therapeutic treatment plan of the subject.

In some embodiments, the diagnostic process is performed by a diagnostic machine learning classifier trained on a subject population. The therapeutic process may be performed by a therapeutic machine learning classifier trained on at least a portion of the subject population. The diagnostic process may further comprise providing feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games, or software features.

In some embodiments, the subject has a risk selected from the group consisting of a behavioral disorder, neurological disorder, and a mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability. The diagnostic process may be performed by an adult to perform an assessment or provide data for an assessment of a child or juvenile. The diagnostic process may enable a caregiver or family member to perform an assessment or provide data for an assessment of the subject.

Another aspect of the present disclosure provides therapeutic systems to treat a subject with a personal therapeutic treatment plan. An exemplary system may comprise a processor comprising software instructions for a diagnostic module to receive data from the subject and output diagnostics data for the subject and a therapeutic module to receive the diagnostic data and output the personal therapeutic treatment plan for the subject. The diagnostic module may be configured to receive updated subject data from the subject in response to a therapy of the subject and generate an updated diagnostic data from the subject. The therapeutic module may be configured to receive the updated diagnostic data and output an updated personal treatment plan for the subject in response to the diagnostic data and the updated diagnostic data.

In some embodiments, the updated subject data is received in response to a feedback data that identifies relative levels of efficacy, compliance, and response resulting from the personal therapeutic treatment plan.

In some embodiments, the personal therapeutic treatment plan comprises digital therapeutics. The digital therapeutics may comprise instructions, feedback, activities, or interactions provided to the subject or caregiver. The digital therapeutics may be provided with a mobile device.

In some embodiments, the diagnostics data and the personal therapeutic treatment plan are provided to a third-party system. The third-party system may comprise a computer system of a health care professional or a therapeutic delivery system.

In some embodiments, the diagnostic module comprises machine learning, a classifier, artificial intelligence, or statistical modeling based on a subject population to determine the diagnostic data. The therapeutic module may comprise machine learning, a classifier, artificial intelligence, or statistical modeling based on at least a portion the subject population to determine the personal therapeutic treatment plan of the subject.

In some embodiments, the diagnostic module comprises a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features of the system.

In some embodiments, the diagnostic module is configured for an adult to perform an assessment or provide data for an assessment of a child or juvenile.

In some embodiments, the diagnostic module is configured for a caregiver or family member to perform an assessment or provide data for an assessment of the subject.

In some embodiments, the subject has a risk selected from the group consisting of a behavioral, neurological and mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

Aspects of the present disclosure also provide methods of treating a subject with a personal therapeutic treatment plan. An exemplary method may comprise a diagnostic process of receiving data from the subject and outputting diagnostics data for the subject and a therapeutic process of receiving the diagnostic data and outputting the personal therapeutic treatment plan for the subject. The diagnostic process may comprise receiving updated subject data from the subject in response to a therapy of the subject and generating an updated diagnostic data from the subject. The therapeutic process may comprise receiving the updated diagnostic data and outputting an updated personal treatment plan for the subject in response to the diagnostic data and the updated diagnostic data.

In some embodiments, the updated subject data is received in response to a feedback data that identifies relative levels of efficacy, compliance, and response resulting from the personal therapeutic treatment plan.

In some embodiments, the personal therapeutic treatment plan comprises digital therapeutics. The digital therapeutics may comprise instructions, feedback, activities, or interactions provided to the subject or caregiver. The digital therapeutics may be provided with a mobile device.

In some embodiments, the method further comprises providing the diagnostics data and the personal therapeutic treatment plan to a third-party system. The third-party system may comprise a computer system of a health care professional or a therapeutic delivery system.

In some embodiments, the diagnostic process is performed by a process selected from the group consisting of machine learning, a classifier, artificial intelligence, or statistical modeling based on a subject population to determine the diagnostic data. The therapeutic process may be performed by a process selected from the group consisting of machine learning, a classifier, artificial intelligence, or statistical modeling based on at least a portion the subject population to determine the personal therapeutic treatment plan of the subject.

In some embodiments, the diagnostic process is performed by a diagnostic machine learning classifier trained on a subject population. The therapeutic process may be performed by a therapeutic machine learning classifier trained on at least a portion of the subject population. The diagnostic process may comprise providing feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features.

In some embodiments, the diagnostic process is performed by an adult to perform an assessment or provide data for an assessment of a child or juvenile.

In some embodiments, the diagnostic process enables a caregiver or family member to perform an assessment or provide data for an assessment of the subject.

In some embodiments, the subject has a risk selected from the group consisting of a behavioral disorder, neurological disorder, and mental health disorder.

In some embodiments, the risk is selected from the group consisting of autism, autistic spectrum, attention deficit disorder, depression, obsessive compulsive disorder, schizophrenia, Alzheimer's disease, dementia, attention deficit hyperactive disorder, and speech and learning disability.

Aspects of the present disclosure also provide therapeutic systems to treat a subject with a personal therapeutic treatment plan. An exemplary system may comprise a processor comprising software instructions for a diagnostic module to receive data from the subject and output diagnostics data for the subject and a therapeutic module to receive the diagnostic data and output the personal therapeutic treatment plan for the subject. The diagnostic module may be configured to generate the diagnostics data by (1) receiving a plurality of answers to a plurality of asked questions among a plurality of questions, the plurality of answers corresponding to clinical characteristics of the subject related to a developmental progress of the subject, a plurality of remaining unasked questions of the plurality of questions comprising a most predictive next question, (2) determining the developmental progress of the subject based on the plurality of answers, and (3) identifying the most predictive next question among the plurality of remaining unasked questions, in response to a determination of the developmental progress of the subject.

In some embodiments, the diagnostic module comprises a preprocessing module, a training module, and a prediction module. The data processing module may extract training data from a database or a user, apply a transformation to standardize the training data, and pass the standardized training data to the training module. The training module may construct an assessment model based on the standardized training data. The prediction module may generate a predicted classification of the subject.

In some embodiments, the training module utilizes a machine learning algorithm to construct and train the assessment model.

In some embodiments, the prediction module is configured to generate the predicted classification of the subject by fitting new data to the assessment model, the new data being standardized by the preprocessing module. The prediction module may check whether the fitting of the new data generates a prediction of a specific disorder within a confidence interval exceeding a threshold value.

In some embodiments, the prediction module comprises a question recommendation module. The question recommendation module may be configured to identify, select or recommend the most predictive next question to be asked with the subject, based on the plurality of answers to the plurality of asked questions, so as to reduce a length of assessment. The question recommendation module may select a candidate question for recommendation as the next question to be presented to the subject. The question recommendation module may evaluate an expected feature importance of each one of the candidate questions. The question recommendation module may select a most predictive next question from the candidate questions, based on the expected feature importance of each one of the candidate questions. The expected feature importance of each one of the candidate questions may be determined with an expected feature importance determination algorithm. The assessment model may comprise a Random Forest classifier.

In some embodiments, the personal therapeutic treatment plan comprises digital therapeutics. The digital therapeutics may comprise instructions, feedback, activities, or interactions provided to the subject or caregiver. The digital therapeutics may be provided with a mobile device.

In some embodiments, the diagnostics data and the personal therapeutic treatment plan are provided to a third-party system. The third-party system may comprise a computer system of a health care professional.

In some embodiments, the diagnostic module is configured to receive updated subject data from the subject in response to a feedback data of the subject and generate updated diagnostic data. The therapeutic module may be configured to receive the updated diagnostic data and output an updated personal treatment plan for the subject in response to the diagnostic data and the updated diagnostic data. The updated subject data may be received in response to a feedback data that identifies relative levels of efficacy, compliance, and response resulting from the personal therapeutic treatment plan.

In some embodiments, the diagnostic module comprises instructions selected from the group consisting of machine learning, a classifier, artificial intelligence, and statistical modeling based on a subject population to determine the diagnostic data. The therapeutic module may comprise instructions selected from the group consisting of machine learning, a classifier, artificial intelligence, or statistical modeling based on at least a portion the subject population to determine the personal therapeutic treatment plan of the subject.

In some embodiments, the diagnostic module comprises a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features of the system.

In some embodiments, the subject has a risk selected from the group consisting of a behavioral disorder, neurological disorder and a mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

In some embodiments, the diagnostic module is configured for an adult to perform an assessment or provide data for an assessment of a child or juvenile.

In some embodiments, the diagnostic module is configured for a caregiver or family member to perform an assessment or provide data for an assessment of the subject.

Aspects of the present disclosure provide methods of treating a subject with a personal therapeutic treatment plan. An exemplary system may comprise a diagnostic process of receiving data from the subject and outputting diagnostics data for the subject and a therapeutic process of receiving the diagnostic data and outputting the personal therapeutic treatment plan for the subject. The diagnostic process may comprise generating the diagnostics data by (1) receiving a plurality of answers to a plurality of asked questions among a plurality of questions, the plurality of answers corresponding to clinical characteristics of the subject related to a developmental progress of the subject, a plurality of remaining unasked questions of the plurality of questions comprising a most predictive next question, (2) determining the developmental progress of the subject based on the plurality of answers, and (3) identifying the most predictive next question among the plurality of remaining unasked questions, in response to a determination of the developmental progress of the subject.

In some embodiments, the diagnostic process comprises a preprocessing process, a training process, and a prediction process. The data processing process may extract training data from a database or a user, apply one or more transformations to standardize the training data, and pass the standardized training data to the training process. The training process may construct an assessment model based on the standardized training data. The prediction process may generate a predicted classification of the subject.

In some embodiments, the training process utilizes a machine learning algorithm to construct and train the assessment model.

In some embodiments, the prediction process generates the predicted classification of the subject by fitting new data to the assessment model, the new data being standardized by the preprocessing process. The prediction process may check whether the fitting of the new data generates a prediction of one or more specific disorders within a confidence interval exceeding a threshold value.

In some embodiments, the prediction process comprises a question recommendation process. The question recommendation process may identify, select, or recommend the most predictive next question to be asked with the subject, based on the plurality of answers to the plurality of asked questions, so as to reduce a length of assessment. The question recommendation process may select one or more candidate questions for recommendation as the next question to be presented to the subject. The question recommendation process may evaluate an expected feature importance of each one of the candidate questions. The question recommendation process may select one or more most predictive next question from the candidate questions, based on the expected feature importance of each one of the candidate questions. The expected feature importance of each one of the candidate questions may be determined with an expected feature importance determination algorithm.

In some embodiments, the assessment process comprises a Random Forest classifier.

In some embodiments, the personal therapeutic treatment plan comprises digital therapeutics. The digital therapeutics comprises instructions, feedback, activities, or interactions provided to the subject or caregiver. The digital therapeutics may be provided with a mobile device.

In some embodiments, the method may further comprise providing the diagnostics data and the personal therapeutic treatment plan to a third-party system. The third-party system may comprise a computer system of a health care professional.

In some embodiments, the diagnostic process may comprise receiving updated subject data from the subject in response to a feedback data of the subject and generating updated diagnostic data. The therapeutic process may comprise receiving the updated diagnostic data and outputting an updated personal treatment plan for the subject in response to the diagnostic data and the updated diagnostic data. The updated subject data may be received in response to a feedback data that identifies relative levels of efficacy, compliance, and response resulting from the personal therapeutic treatment plan.

In some embodiments, the diagnostic process is performed by a process selected from the group consisting of machine learning, a classifier, artificial intelligence, or statistical modeling based on a subject population to determine the diagnostic data. The therapeutic process may be performed by a process selected from the group consisting of machine learning, a classifier, artificial intelligence, or statistical modeling based on at least a portion the subject population to determine the personal therapeutic treatment plan of the subject.

In some embodiments, the diagnostic process is performed by a diagnostic machine learning classifier trained on a subject population. The therapeutic process may be performed by a therapeutic machine learning classifier trained on at least a portion of the subject population. The diagnostic process may comprise providing feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features of the system.

In some embodiments, the subject has a risk selected from the group consisting of a behavioral disorder, neurological disorder, and a mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

In some embodiments, the diagnostic process is performed by an adult to perform an assessment or provide data for an assessment of a child or juvenile.

In some embodiments, the diagnostic process enables a caregiver or family member to perform an assessment or provide data for an assessment of the subject.

Aspects of the present disclosure provide therapeutic systems to treat a subject having a behavioral, neurological, or mental health disorder among two or more related behavioral, neurological, or mental health disorders with a personal therapeutic treatment plan. An exemplary system may comprise a processor comprising software instructions for a diagnostic module to receive data from the subject and output diagnostics data for the subject and a therapeutic module to receive the diagnostic data and output the personal therapeutic treatment plan for the subject. The diagnostic module may be configured to generate the diagnostics data by (1) receiving a plurality of answers to a plurality of asked questions among a plurality of questions, the plurality of answers corresponding to clinical characteristics of the subject related to two or more related behavioral, neurological or mental health disorders, a plurality of remaining unasked questions of the plurality of questions comprising a most predictive next question, (2) determining, based on the plurality of answers, whether the subject is at greater risk of a first developmental disorder or a second developmental disorder of the two or more behavioral, neurological or mental health disorders, and (3) identifying the most predictive next question among the plurality of remaining unasked questions, in response a determination of the subject as at greater risk of a first developmental disorder or a second developmental disorder of the two or more related behavioral, neurological or mental health disorders.

In some embodiments, a question that is most predictive of the first developmental disorder is identified as the most predictive next question in response to a determination of the subject as at greater risk of the first developmental disorder.

In some embodiments, a question that is most predictive of the second developmental disorder is identified as the most predictive next question in response to a determination of the subject as at greater risk of the second developmental disorder.

In some embodiments, the system further comprises a memory having an assessment model stored thereon. The assessment model may comprise statistical correlations between a plurality of clinical characteristics and clinical diagnoses of the two or more behavioral, neurological or mental health disorders.

In some embodiments, the processor is further configured with instructions to determine whether the subject is at greater risk of the first developmental disorder or the second developmental disorder in response to the assessment model.

In some embodiments, the processor is configured with instructions to display the question and the most predictive next question.

In some embodiments, the processor comprises instructions to identify the most predictive next question in response to the plurality of answers corresponding to the plurality of clinical characteristics of the subject.

In some embodiments, the processor is configured with instructions to identify the most predictive next question in response to an estimated predictive utility of each remaining question.

In some embodiments, the processor is configured with sufficient statistics to identify the most predictive next question that is most predictive of the first developmental disorder. In some embodiments, the processor is configured with sufficient statistics of a machine learning algorithm configured in response to a plurality of clinically assessed subject populations in order to identify the most predictive next question that is most predictive of greater risk of the first developmental disorder.

In some embodiments, the processor is configured with instructions to identify the most predictive next question in response to an estimated predictive utility of the most predictive next question with respect to each of the two or more behavioral, neurological or mental health disorders.

In some embodiments, the processor is configured to determine the subject as at risk of the developmental disorder with a confidence interval selected from the group consisting of at least 85%, and a sensitivity and specificity of at least 85%.

In some embodiments, the personal therapeutic treatment plan comprises digital therapeutics. The digital therapeutics may comprise instructions, feedback, activities, or interactions provided to the subject or caregiver. The digital therapeutics may be provided with a mobile device.

In some embodiments, the diagnostics data and the personal therapeutic treatment plan are provided to a third-party system. The third-party system may comprise a computer system of a health care professional.

In some embodiments, the diagnostic module is configured to receive updated subject data from the subject in response to a feedback data of the subject and generate updated diagnostic data. The therapeutic module may be configured to receive the updated diagnostic data and output an updated personal treatment plan for the subject in response to the diagnostic data and the updated diagnostic data. The updated subject data may be received in response to a feedback data that identifies relative levels of efficacy, compliance and response resulting from the personal therapeutic treatment plan.

In some embodiments, the diagnostic module comprises instructions selected from the group consisting of machine learning, a classifier, artificial intelligence, or statistical modeling based on a subject population to determine the diagnostic data. The therapeutic module may comprise instructions selected from the group consisting of machine learning, a classifier, artificial intelligence, or statistical modeling based on at least a portion the subject population to determine the personal therapeutic treatment plan of the subject.

In some embodiments, the diagnostic module comprises a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games or software features of the system.

In some embodiments, the subject has a risk of a behavioral, neurological or mental health disorder. The behavioral, neurological, or mental health disorder may comprise at least one of autism, autistic spectrum, attention deficit disorder, attention deficit hyperactive disorder, and speech and learning disability.

In some embodiments, the diagnostic module is configured for an adult to perform an assessment or provide data for an assessment of a child or juvenile.

In some embodiments, the diagnostic module is configured for a caregiver or family member to perform an assessment or provide data for an assessment of the subject.

Aspects of the present disclosure also provide methods of treating a subject having a behavioral, neurological, or mental health disorder among two or more related behavioral, neurological, or mental health disorders with a personal therapeutic treatment plan. An exemplary method may comprise a diagnostic process of receiving data from the subject and outputting diagnostics data for the subject and a therapeutic process of receiving the diagnostic data and outputting the personal therapeutic treatment plan for the subject. The diagnostics data may be generated by (1) receiving a plurality of answers to a plurality of asked questions among a plurality of questions, the plurality of answers corresponding to clinical characteristics of the subject related to two or more related behavioral, neurological or mental health disorders, a plurality of remaining unasked questions of the plurality of questions comprising a most predictive next question, (2) determining, based on the plurality of answers, whether the subject is at greater risk of a first developmental disorder or a second developmental disorder of the two or more behavioral, neurological or mental health disorders, and (3) identifying the most predictive next question among the plurality of remaining unasked questions, in response a determination of the subject as at greater risk of a first developmental disorder or a second developmental disorder of the two or more related behavioral, neurological or mental health disorders.

In some embodiments, in a question that is most predictive of the first developmental disorder is identified as the most predictive next question in response to a determination of the subject as at greater risk of the first developmental disorder.

In some embodiments, a question that is most predictive of the second developmental disorder is identified as the most predictive next question in response to a determination of the subject as at greater risk of the second developmental disorder.

In some embodiments, the method may further comprise an assessment model storing process. The assessment model may comprise statistical correlations between a plurality of clinical characteristics and clinical diagnoses of the two or more behavioral, neurological, or mental health disorders.

In some embodiments, the method further comprises determining whether the subject is at greater risk of the first developmental disorder or the second developmental disorder in response to the assessment model.

In some embodiments, the method further comprises displaying the question and the most predictive next question.

In some embodiments, the method further comprises identifying the most predictive next question in response to the plurality of answers corresponding to the plurality of clinical characteristics of the subject.

In some embodiments, the method further comprises identifying the most predictive next question in response to an estimated predictive utility of each remaining question.

In some embodiments, the diagnostic process comprises providing sufficient statistics identify the most predictive next question that is most predictive of the first developmental disorder.

In some embodiments, the diagnostic process comprises providing sufficient statistics of a machine learning algorithm configured in response to a plurality of clinically assessed subject populations in order to identify the most predictive next question that is most predictive of greater risk of the first developmental disorder.

In some embodiments, the diagnostic process comprises identifying the most predictive next question in response to an estimated predictive utility of the most predictive next question with respect to each of the two or more behavioral, neurological or mental health disorders.

In some embodiments, the diagnostic process comprises determining the subject as at risk of the developmental disorder with a confidence interval selected from the group consisting of at least 85%, and a sensitivity and specificity of at least 85%.

In some embodiments, the personal therapeutic treatment plan comprises digital therapeutics. The digital therapeutics comprises instructions, feedback, activities, or interactions provided to the subject or caregiver. The digital therapeutics may be provided with a mobile device.

In some embodiments, the method further comprises providing the diagnostics data and the personal therapeutic treatment plan to a third-party system. The third-party system may comprise a computer system of a health care professional.

In some embodiments, the diagnostic process comprises receiving updated subject data from the subject in response to a feedback data of the subject and generating updated diagnostic data. The therapeutic process may comprise receiving the updated diagnostic data and outputting an updated personal treatment plan for the subject in response to the diagnostic data and the updated diagnostic data. The updated subject data may be received in response to a feedback data that identifies relative levels of efficacy, compliance and response resulting from the personal therapeutic treatment plan.

In some embodiments, the diagnostic process is performed by a process selected from the group consisting of machine learning, a classifier, artificial intelligence, and statistical modeling based on a subject population to determine the diagnostic data.

In some embodiments, the therapeutic process is performed by a process selected from the group consisting of machine learning, a classifier, artificial intelligence, and statistical modeling based on at least a portion the subject population to determine the personal therapeutic treatment plan of the subject.

In some embodiments, the diagnostic process is performed by a diagnostic machine learning classifier trained on a subject population. The therapeutic process may be performed by a therapeutic machine learning classifier trained on at least a portion of the subject population. The diagnostic process may comprise providing feedback to the therapeutic module based on performance of the personal therapeutic treatment plan.

In some embodiments, the data from the subject comprises at least one of the subject and caregiver video, audio, responses to questions or activities, and active or passive data streams from user interaction with activities, games, or software features of the system.

In some embodiments, the subject has a risk selected from the group consisting of a behavioral disorder, a neurological disorder and a mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

In some embodiments, the diagnostic process is performed by an adult to perform an assessment or provide data for an assessment of a child or juvenile.

In some embodiments, the diagnostic process enables a caregiver or family member to perform an assessment or provide data for an assessment of the subject.

Aspects of the present disclosure may also provide a tangible medium configured with instructions, that when executed cause a processor to: receive updated subject data in response to the therapy of the subject and output an updated personal treatment plan for the subject in response to the updated subject data.

In some embodiments, the diagnostic module and the therapeutic module each comprises a classifier trained on a population not comprising the subject.

In some embodiments, the processor comprises a plurality of processors.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
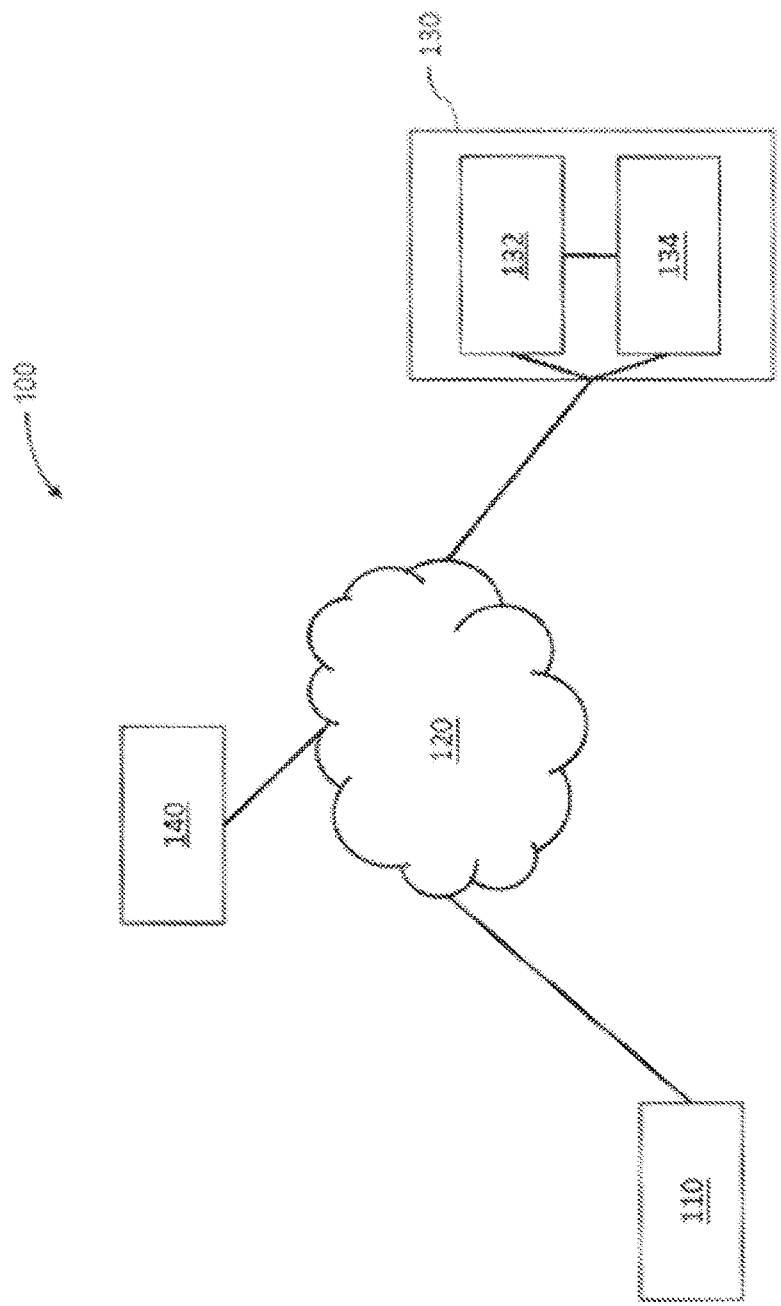
FIG. 1A illustrates an exemplary system diagram for a digital personalized medicine platform.

In an aspect, the digital personalized medicine system comprises digital devices with processors and associated software configured to: receive data to assess and diagnose a patient; capture interaction and feedback data that identify relative levels of efficacy, compliance and response resulting from the therapeutic interventions; and perform data analysis, including at least one or machine learning, artificial intelligence, and statistical models to assess user data and user profiles to further personalize, improve or assess efficacy of the therapeutic interventions.

In some instances, the system is configured to use digital diagnostics and digital therapeutics. Digital diagnostics and digital therapeutics can comprise a system or methods comprising collecting digital information and processing and analyzing the provided data to improve the medical, psychological, or physiological state of an individual. A digital therapeutic system can apply software based learning to analyze user data, monitor and improve the diagnoses and therapeutic interventions provided by the system.

Digital diagnostics in the system can comprise of data and meta-data collected from the patient, or a caregiver, or a party that is independent of the individual being assessed. In some instances the collected data can comprise monitoring behaviors, observations, judgements, or assessments may be made by a party other than the individual. In further instances the assessment can comprise an adult performing an assessment or provide data for an assessment of a child or juvenile.

Data sources can comprise either active or passive sources, in digital format via one or more digital devices such as mobile phones, video capture, audio capture, activity monitors, or wearable digital monitors. Examples of active data collection comprise devices, systems or methods for tracking eye movements, recording body or appendage movement, monitoring sleep patterns, recording speech patterns. In some instances, the active sources can include audio feed data source such as speech patterns, lexical/syntactic patterns (for example, size of vocabulary, correct/incorrect use of pronouns, correct/incorrect inflection and conjugation, use of grammatical structures such as active/passive voice etc., and sentence flow), higher order linguistic patterns (for example, coherence, comprehension, conversational engagement, and curiosity), touch-screen data source (for example, fine-motor function, dexterity, precision and frequency of pointing, precision and frequency of swipe movement, and focus/attention span), and video recording of subject's face during activity (for example, quality/quantity of eye fixations vs saccades, heat map of eye focus on the screen, focus/attention span, variability of facial expression, and quality of response to emotional stimuli). Passive data collection can comprise devices, systems, or methods for collecting data from the user using recording or measurements derived from mobile applications, toys with embed sensors or recording units. In some instances, the passive source can include sensors embedded in smart toys (for example, fine motor function, gross motor function, focus/attention span and problem solving skills) and wearable devices (for example, level of activity, quantity/quality of rest).

The data used in the diagnosis and treatment can come from a plurality of sources, and may comprise a combination of passive and active data collection gathered from one device such as a mobile device with which the user interacts, or other sources such as microbiome sampling and genetic sampling of the subject.

The methods and apparatus disclose herein are well suited for the diagnosis and digital therapeutic treatment of cognitive and developmental disorders, mood and mental illness, and neurodegenerative diseases. Examples of cognitive and developmental disorders include speech and learning disorders, intelligence quotient ("IQ"), non-verbal IQ and verbal IQ and other disorders as described herein. Examples of mood and mental illness disorders, which can effect children and adults, include behavioral disorders, mood disorders, depression, attention deficit hyperactivity disorder ("ADHD"), obsessive compulsive disorder ("OCD"), schizophrenia, and substance such as eating disorders and substance abuse. Examples of neurodegenerative diseases include age related cognitive decline, cognitive impairment progressing to Alzheimer's and senility, Parkinson's disease and Huntington's disease, and amyotrophic lateral sclerosis ("ALS"). The methods and apparatus disclosed herein are capable of digitally diagnosing and treating children and continuing treatment until the subject becomes an adult, and can provide lifetime treatment based on personalized profiles.

The digital diagnosis and treatment as described herein is well suited for behavioral intervention coupled with biological or chemical therapeutic treatment. By gathering user interaction data as described herein, feedback effective therapies can be provided for combinations of behavioral intervention data pharmaceutical and biological treatments.

The mobile devices as describe herein may comprise sensors to collect data of the subject that can be used as part of the feedback loop so as to improve outcomes and decrease reliance on user input. The mobile device may comprise a passive or active sensors as described herein to collect data of the subject subsequent to treatment. The same mobile device or a second mobile device, such as an iPad™ or iPhone™ or similar device, may comprise a software application that interacts with the user to tell the user what to do in improve treatment on a regular basis, e.g. day by day, hour by hour, etc. The user mobile device can be configured to send notifications to the user in response to treatment progress. The mobile device may comprise a drug delivery device configured to monitor deliver amounts of a therapeutic agent delivered to the subject.

The methods and apparatus disclosed herein are well suited for treatment of both parents and children, for example. Both a parent and a child can receive separate treatments as described herein. For example, neurological condition of the parent can be monitored and treated, and the developmental progress of the child monitored and treated.

The mobile device used to acquire data of the subject can be configured in many ways and may combine a plurality of devices, for example. Sleep patterns can be related to autism, for example, and sleep data acquired and used as input to the diagnostic and therapeutic modules as described herein. The mobile device may comprise a mobile wearable for sleep monitoring for a child, which can be provide as input for diagnosis and treatment and may comprise a component of the feedback loop as described herein.

Many types of sensor, biosensors and data can be used to gather data of the subject and input into the diagnosis and treatment of the subject. For example, work in relation to embodiments suggests that microbiome data can be useful for the diagnosis and treatment of Autism. The microbiome data can be collected in many ways known to one of ordinary skill in the art, and may comprise data selected from a stool sample, intestinal lavage, or other sample of the flora of the subject's intestinal track. Genetic data can also be acquired an input into the diagnostic and therapeutic modules. The genetic data may comprise full genomic sequencing of the subject, of sequencing and identification of specific markers.

The diagnostic and therapeutic modules as disclosed herein can receive data from a plurality of sources, such as data acquired from the group consisting of genetic data, floral data, a sleep sensor, a wearable anklet sleep monitor, a booty to monitor sleep, and eye tracking of the subject. The eye tracking can be performed in many ways to determine the direction and duration of gaze. The tracking can be done glasses, helmets other sensors for direction and duration of gaze. The data can be acquired with any combination of games, video games, captured video of the subject and these can be used to determine facial expression and gaze of the subject. This data can be acquired and provided to the therapeutic module and diagnostic module as described herein before, during and after treatment, in order to initially diagnose the subject, determine treatment of the subject, modify treatment of the subject, and monitor the subject subsequent to treatment.

The visual gaze, duration of gaze and facial expression information can be acquired with methods and apparatus known to one of ordinary skill in the art, and acquired an input into the diagnostic and therapeutic modules. The data can be acquired with an app comprising software instructions, which can be downloaded. For example, facial processing has been described by Gloarai et al. "Autism and the development of face processing", Clinical Neuroscience Research 6 (2006) 145-160. An autism research group at Duke University has been conducting the Autism and beyond research study with a software app downloaded onto mobile devices as described on the web page at autismandbeyond.researchkit.duke.edu. Data from such devices is particularly well suited for combination in accordance with the present disclosure. Facial recognition data and gaze data can be input into the diagnostic and therapeutic modules as described herein.

The classifiers as disclosed herein are particularly well suited for combination with this data to provide improved therapy and treatment. The data can be stratified and used with a feedback loop as described herein. For example, the feedback data can be used in combination with a drug therapy to determine differential responses and identify responders and non-responders. Alternatively or in combination, the feedback data can be combined with non-drug therapy, such as behavioral therapy.

With regards to genetics, recent work suggests that some people may have genetics that make them more susceptible to Autism. The genetic composition of the subject may render the subject more susceptible to environmental influences, which can result symptoms and may influence the severity of symptoms. The environmental influence may comprise an insult from a toxin, virus or other substance, for example. Without being bound by any particular theory, this may result in mechanisms that change the regulation of expression genes. The change in expression of genes may be related to change in gastro-intestinal ("GI") flora, and these changes in flora may affect symptoms related to Autism. Alternatively or in combination, an insult to the intestinal microbiome may result in a change in the microbiome of the subject, resulting in the subject having less than ideal homeostasis, which may affect associated symptoms related to Autism. The inventors note that preliminary studies with *B. fragilis* conducted by Sarkis K. Mazmanian and others, suggest changes in this micro-organism can be related to autism and the development of autisms. (See also, "Gut Bacteria May Play a Role in Autism" by Melinda Wenner Moyer, *Scientific American*, Sep. 1, 2014)

The digital diagnostic uses the data collected by the system about the patient, which may include complimentary diagnostic data captured outside the digital diagnostic, with analysis from tools such as machine learning, artificial intelligence, and statistical modeling to assess or diagnose the patient's condition. The digital diagnostic can also provide assessment of a patient's change in state or performance, directly or indirectly via data and meta-data that can be analyzed by tools such as machine learning, artificial intelligence, and statistical modeling to provide feedback into the system to improve or refine the diagnoses and potential therapeutic interventions.

Data assessment and machine learning from the digital diagnostic and corresponding responses, or lack thereof, from the therapeutic interventions can lead to the identification of novel diagnoses for patients and novel therapeutic regimens for both patents and caregivers.

Types of data collected and utilized by the system can include patient and caregiver video, audio, responses to questions or activities, and active or passive data streams from user interaction with activities, games or software features of the system, for example. Such data can also include meta-data from patient or caregiver interaction with the system, for example, when performing recommended activities. Specific meta-data examples include data from a user's interaction with the system's device or mobile app that captures aspects of the user's behaviors, profile, activities, interactions with the software system, interactions with games, frequency of use, session time, options or features selected, and content and activity preferences. Data may also include data and meta-data from various third party devices such as activity monitors, games or interactive content.

Digital therapeutics as described herein can comprise of instructions, feedback, activities or interactions provided to the patient or caregiver by the system. Examples include suggested behaviors, activities, games or interactive sessions with system software and/or third party devices (for example, the Internet of Things "IoT" enabled therapeutic devices as understood by one of ordinary skill in the art).

FIG. 1A illustrates a system diagram for a digital personalized medicine platform 100 for providing diagnosis and therapy related to behavioral, neurological or mental health disorders. The platform 100 can provide diagnosis and treatment of pediatric cognitive and behavioral conditions associated with developmental delays, for example. A user digital device 110—for example, a mobile device such as a smart phone, an activity monitors, or a wearable digital monitor—records data and metadata related to a patient. Data may be collected based on interactions of the patient with the device, as well as based on interactions with caregivers and health care professionals. The data may be collected actively, such as by administering tests, recording speech and/or video, and recording responses to diagnostic questions. The data may also be collected passively, such as by monitoring online behavior of patients and caregivers, such as recording questions asked and topics investigated relating to a diagnosed developmental disorder.

The digital device 110 is connected to a computer network 120, allowing it to share data with and receive data from connected computers. In particular, the device can communicate with personalized medical system 130, which comprises a server configured to communicate with digital device 110 over the computer network 120. Personalized medical system 130 comprises a diagnosis module 132 to provide initial and incremental diagnosis of a patient's developmental status, as well as a therapeutic module 134 to provide personalized therapy recommendations in response to the diagnoses of diagnosis module 132.

Each of diagnosis modules 132 and 134 communicate with the user digital device 110 during a course of treatment. The diagnosis module provides diagnostic tests to and receives diagnostic feedback from the digital device 110, and uses the feedback to determine a diagnosis of a patient. An initial diagnosis may be based on a comprehensive set of tests and questions, for example, while incremental updates may be made to a diagnosis using smaller data samples. For example, the diagnostic module may diagnose autism-related speech delay based on questions asked to the caregiver and tests administered to the patient such as vocabulary or verbal communication tests. The diagnosis may indicate a number of months or years delay in speech abilities. Later tests may be administered and questions asked to update this diagnosis, for example showing a smaller or larger degree of delay.

The diagnosis module communicates its diagnosis to the digital device 110, as well as to therapy module 134, which uses the diagnosis to suggest therapies to be performed to treat any diagnosed symptoms. The therapy module 134 sends its recommended therapies to the digital device 110, including instructions for the patient and caregivers to perform the therapies recommended over a given time frame. After performing the therapies over the given time frame, the caregivers or patient can indicate completion of the recommended therapies, and a report can be sent from the digital device 110 to the therapy module 134. The therapy module 134 can then indicate to the diagnosis module 132 that the latest round of therapy is finished, and that a new diagnosis is needed. The diagnostic module 132 can then provide new diagnostic tests and questions to the digital device 110, as well as take input from the therapy module of any data provided as part of therapy, such as recordings of learning sessions or browsing history of caregivers or patients related to the therapy or diagnosed condition. The diagnostic module 132 then provides an updated diagnosis to repeat the process and provide a next step of therapy.

Information related to diagnosis and therapy can also be provided from personalized medical system 130 to a third-party system 140, such as a computer system of a health care professional. The health care professional or other third party can be alerted to significant deviations from a therapy schedule, including whether a patient is falling behind an expected schedule or is improving faster than predicted. Appropriate further action can then be taken by the third party based on this provided information.

Figure 1B:
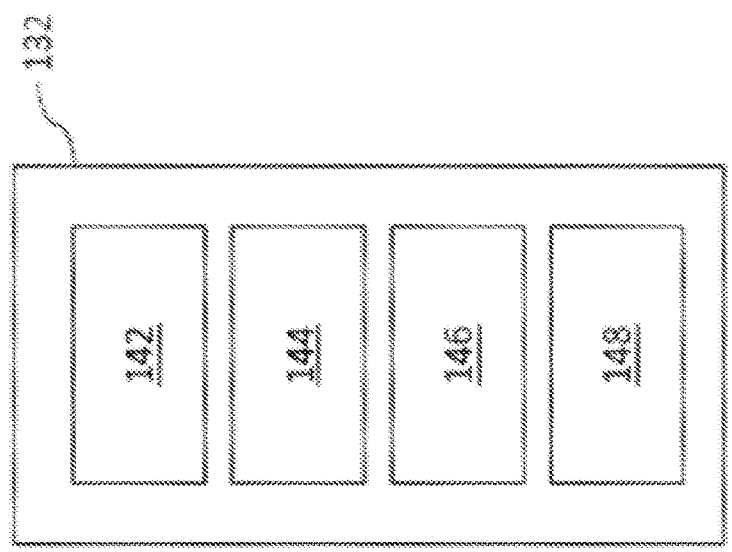
FIG. 1B illustrates a detailed diagram of an exemplary diagnosis module.

FIG. 1B illustrates a detailed diagram of diagnosis module 132. The diagnosis module 132 comprises a test administration module 142 that generates tests and corresponding instructions for administration to a subject. The diagnosis module 132 also comprises a subject data receiving module 144 in which subject data are received, such as test results; caregiver feedback; meta-data from patient and caregiver interactions with the system; and video, audio, and gaming interactions with the system, for example. A subject assessment module 146 generates a diagnosis of the subject based on the data from subject data receiving module 144, as well as past diagnoses of the subject and of similar subjects. A machine learning module 148 assesses the relative sensitivity of each input to the diagnosis to determine which types of measurement provide the most information regarding a patient's diagnosis. These results can be used by test administration module 142 to provide tests which most efficiently inform diagnoses and by subject assessment module 146 to apply weights to diagnosis data in order to improve diagnostic accuracy and consistency. Diagnostic data relating to each treated patient are stored, for example in a database, to form a library of diagnostic data for pattern matching and machine learning. A large number of subject profiles can be simultaneously stored in such a database, for example 10,000 or more.

Figure 1C:
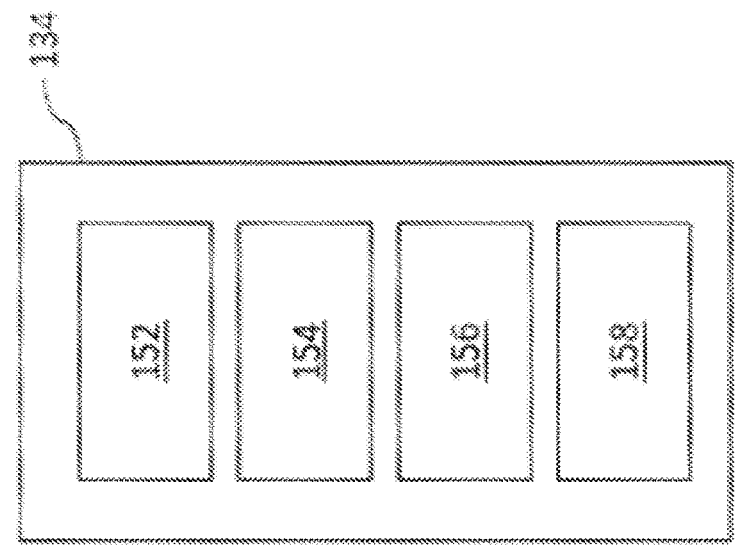
FIG. 1C illustrates a diagram of an exemplary therapy module.

FIG. 1C illustrates a detailed diagram of therapy module 134. Therapy module 134 comprises a therapy assessment module 152 that scores therapies based on their effectiveness. A previously suggested therapy is evaluated based on the diagnoses provided by the diagnostic module both before and after the therapy, and a degree of improvement is determined. This degree of improvement is used to score the effectiveness of the therapy. The therapy may have its effectiveness correlated with particular classes of diagnosis; for example, a therapy may be considered effective for subjects with one type of diagnosis but ineffective for subjects with a second type of diagnosis. A therapy matching module 154 is also provided that compares the diagnosis of the subject from diagnosis module 132 with a list of therapies to determine a set of therapies that have been determined by the therapy assessment module 152 to be most effective at treating diagnoses similar to the subject's diagnosis. Therapy recommendation module 156 then generates a recommended therapy comprising one or more of the therapies identified as promising by the therapy matching module 154, and sends that recommendation to the subject with instructions for administration of the recommended therapies. Therapy tracking module 158 then tracks the progress of the recommended therapies, and determines when a new diagnosis should be performed by diagnosis module 132, or when a given therapy should be continued and progress further monitored. Therapeutic data relating to each patient treated are stored, for example in a database, to form a library of therapeutic data for pattern matching and machine learning. A large number of subject profiles can be simultaneously stored in such a database, for example 10,000 or more. The therapeutic data can be correlated to the diagnostic data of the diagnostic module 132 to allow a matching of effective therapies to diagnoses.

Figure 2:
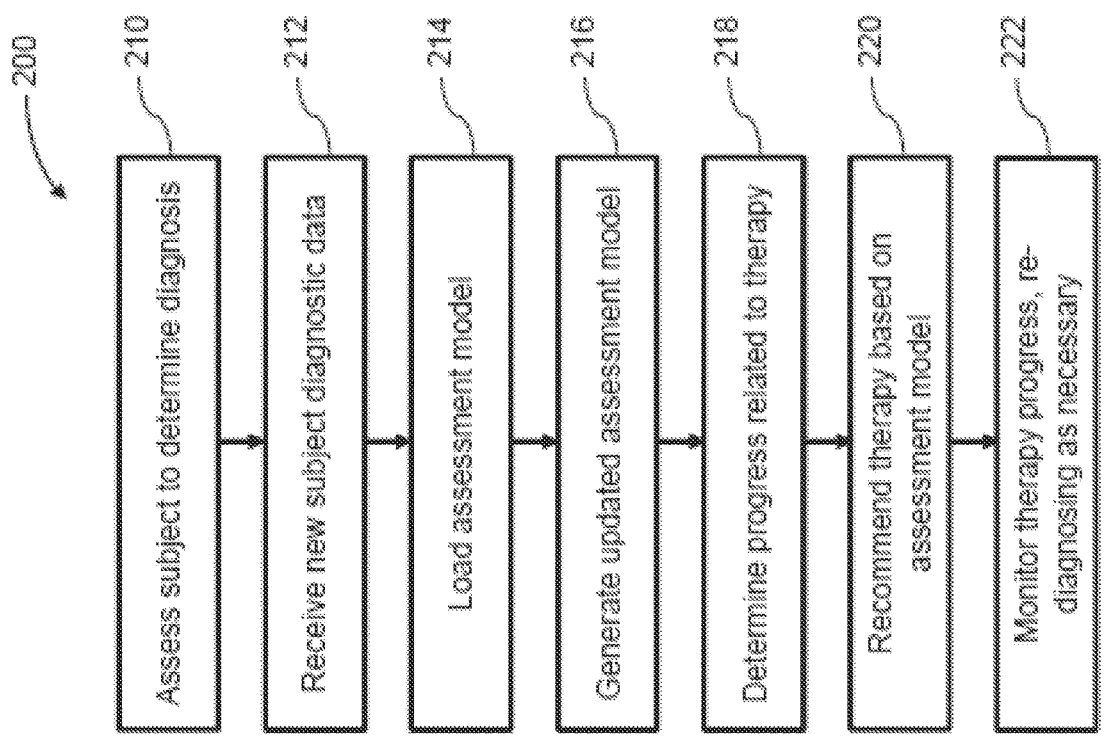
FIG. 2 illustrates an exemplary method for diagnosis and therapy to be provided in a digital personalized medicine platform.

A therapy can comprise a digital therapy. A digital therapy can comprise a single or multiplicity of therapeutic activities or interventions that can be performed by the patient or caregiver. The digital therapeutic can include prescribed interactions with third party devices such as sensors, computers, medical devices and therapeutic delivery systems. Digital therapies can support an FDA approved medical claim, a set of diagnostic codes, a single diagnostic code FIG. 2 illustrates a method 200 for diagnosis and therapy to be provided in a digital personalized medicine platform. The digital personalized medicine platform communicates with a subject, which may include a patient with one or more caregivers, to provide diagnoses and recommend therapies.

In step 210 the diagnosis module assesses the subject to determine a diagnosis, for example by applying diagnostic tests to the subject. The diagnostic tests may be directed at determining a plurality of features and corresponding feature values for the subject. For example, the tests may include a plurality of questions presented to a subject, observations of the subject, or tasks assigned to the subject. The tests may also include indirect tests of the subject, such as feedback from a caregiver of patient performance versus specific behaviors and/or milestones; meta-data from patient and caregiver interactions with the system; and video, audio, and gaming interactions with the system or with third party tools that provide data on patient and caregiver behavior and performance. For initial tests, a more comprehensive testing regimen may be performed, aimed at generating an accurate initial diagnosis. Later testing used to update prior diagnoses to track progress can involve less comprehensive testing and may, for example, rely more on indirect tests such as behavioral tracking and therapy-related recordings and meta-data.

In step 212, the diagnosis module receives new data from the subject. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The feature values may also comprise recorded feedback, meta-data, and system interaction data as described above.

In step 214, the diagnosis module can load a previously saved assessment model from a local memory and/or a remote server configured to store the model. Alternatively, if no assessment model exists for the patient, a default model may be loaded, for example, based on one or more initial diagnostic indications.

In step 216, the new data is fitted to the assessment model to generate an updated assessment model. This assessment model may comprise an initial diagnosis for a previously untreated subject, or an updated diagnosis for a previously treated subject. The updated diagnosis can include a measurement of progress in one or more aspects of a condition, such as memory, attention and joint attention, cognition, behavioral response, emotional response, language use, language skill, frequency of specific behaviors, sleep, socialization, non-verbal communication, and developmental milestones. The analysis of the data to determine progress and current diagnosis can include automated analysis such as question scoring and voice-recognition for vocabulary and speech analysis. The analysis can also include human scoring by analysis reviewing video, audio, and text data.

In step 218, the updated assessment model is provided to the therapy module, which determines what progress has been made as a result of any previously recommended therapy. The therapy module scores the therapy based on the amount of progress in the assessment model, with larger progress corresponding to a higher score, making a successful therapy and similar therapies more likely to be recommended to subjects with similar assessments in the future. The set of therapies available is thus updated to reflect a new assessment of effectiveness, as correlated with the subject's diagnosis.

In step 220, a new therapy is recommended based on the assessment model, the degree of success of the previous therapy, if any, and the scores assigned to a collection of candidate therapies based on previous uses of those therapies with the subject and other subjects with similar assessments. The recommended therapy is sent to the subject for administration, along with instructions of a particular span of time to apply it. For example, a therapy might include a language drill to be performed with the patient daily for one week, with each drill to be recorded in an audio file in a mobile device used by a caregiver or the patient.

In step 222, progress of the new therapy is monitored to determine whether to extend a period of therapy. This monitoring may include periodic re-diagnoses, which may be performed by returning to step 210. Alternatively, basic milestones may be recorded without a full re-diagnosis, and progress may be compared to a predicted progress schedule generated by the therapy module. For example, if a therapy is unsuccessful initially, the therapy module may suggest repeating it one or more times before either re-diagnosing and suggesting a new therapy or suggesting intervention by medical professionals.

Figure 3:
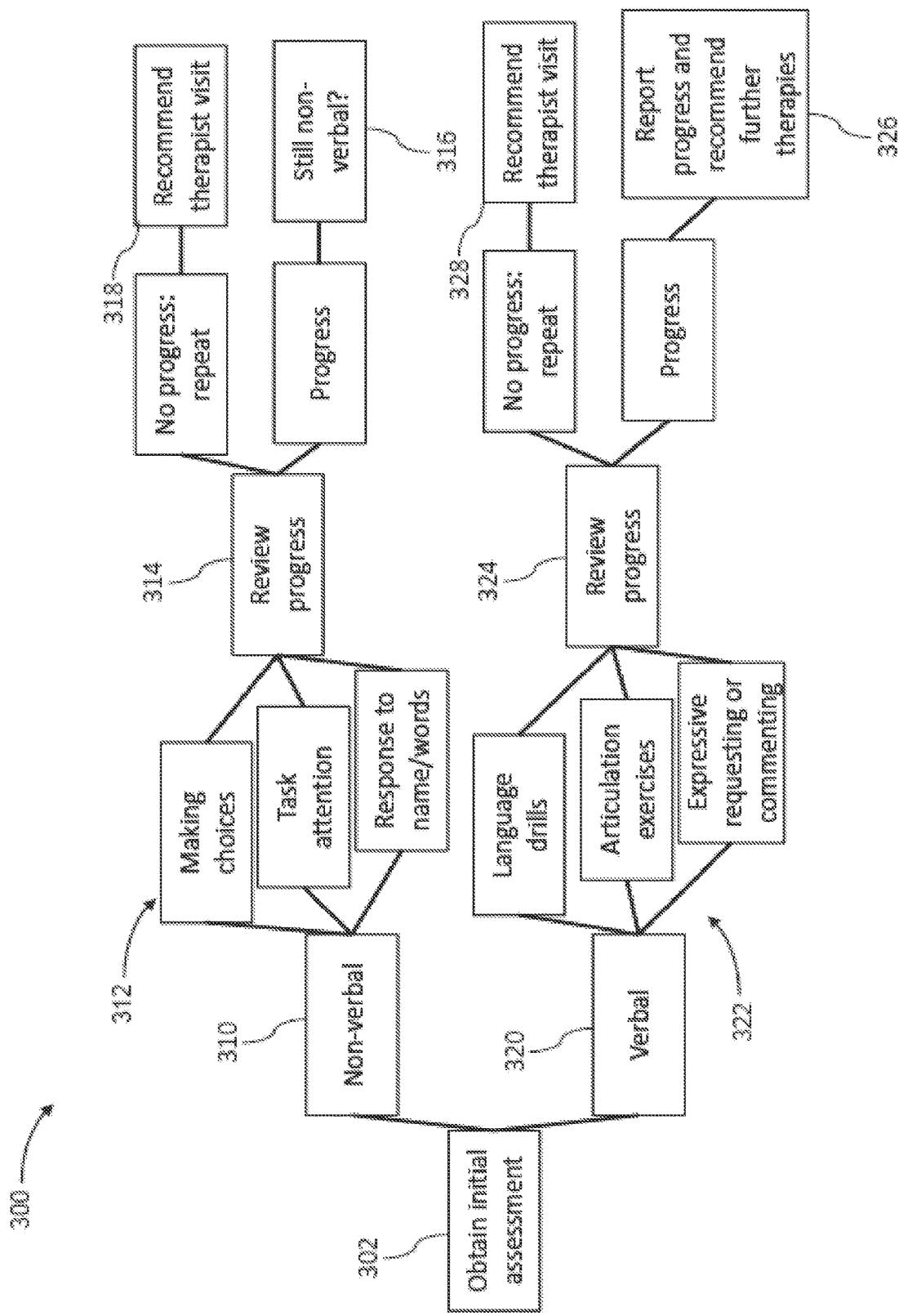
FIG. 3 illustrates an exemplary flow diagram showing the handling of autism-related developmental delay.

FIG. 3 illustrates a flow diagram 300 showing the handling of suspected or confirmed speech and language delay.

In step 302 an initial assessment is determined by diagnosis module 132. The initial assessment can assess the patient's performance in one or more domains, such as speech and language use, and assess a degree and type of developmental delay along a number of axes, as disclosed herein. The assessment can further place the subject into one of a plurality of overall tracks of progress; for example, the subject can be assessed as verbal or nonverbal.

If the subject is determined to be non-verbal, as in step 310, one or more non-verbal therapies 312 can be recommended by the therapy module 134, such as tasks related to making choices, paying attention to tasks, or responding to a name or other words. Further suggestions of useful devices and products that may be helpful for progress may also be provided, and all suggestions can be tailored to the subject's needs as indicated by the subject's diagnosis and progress reports.

While applying the recommended therapies, progress is monitored in step 314 to determine whether a diagnosis has improved at a predicted rate.

If improvement has been measured in step 314, the system determines whether the subject is still non-verbal in step 316; if so, then the system returns to step 310 and generates a new recommended therapy 312 to induce further improvements.

If no improvement is measured in step 314, the system can recommend that the therapy be repeated a predetermined number of times. The system may also recommend trying variations in therapy to try and get better results. If such repetitions and variations fail, the system can recommend a therapist visit in step 318 to more directly address the problems impeding development.

Once the subject is determined to be verbal, as indicated in step 320, verbal therapies 322 can be generated by therapy module 134. For example, verbal therapies 322 can include one or more of language drills, articulation exercises, and expressive requesting or communicating. Further suggestions of useful devices and products that may be helpful for progress may also be provided, and all suggestions can be tailored to the subject's needs as indicated by the subject's diagnosis and progress reports.

As in the non-verbal track, progress in response to verbal therapies is continually monitored in step 324 to determine whether a diagnosis has improved at a predicted rate.

If improvement has been measured in step 324, the system reports on the progress in step 326 and generates a new recommended therapy 322 to induce further improvements.

If no improvement is detected in step 324, the system can recommend that the therapy be repeated a predetermined number of times. The system may also recommend trying variations in therapy to try and get better results. If such repetitions and variations fail, the system can recommend a therapist visit in step 328 to more directly address the problems impeding development.

The steps for non-verbal and verbal therapy can be repeated indefinitely, to the degree needed to stimulate continued learning and progress in the subject, and to prevent or retard regress through loss of verbal skills and abilities. While the specific therapy plan illustrated in FIG. 3 is directed towards pediatric speech and language delay similar plans may be generated for other subjects with developmental or cognitive issues, including plans for adult patients. For example, neurodegenerative conditions and/or age related cognitive decline may be treated with similar diagnosis and therapy schedules, using treatments selected to be appropriate to such conditions. Further conditions that may be treated in adult or pediatric patients by the methods and systems disclosed herein include mood disorders such as depression, OCD, and schizophrenia; cognitive impairment and decline; sleep disorders; addictive behaviors; eating disorders; and behavior related weight management problems.

Figure 4:
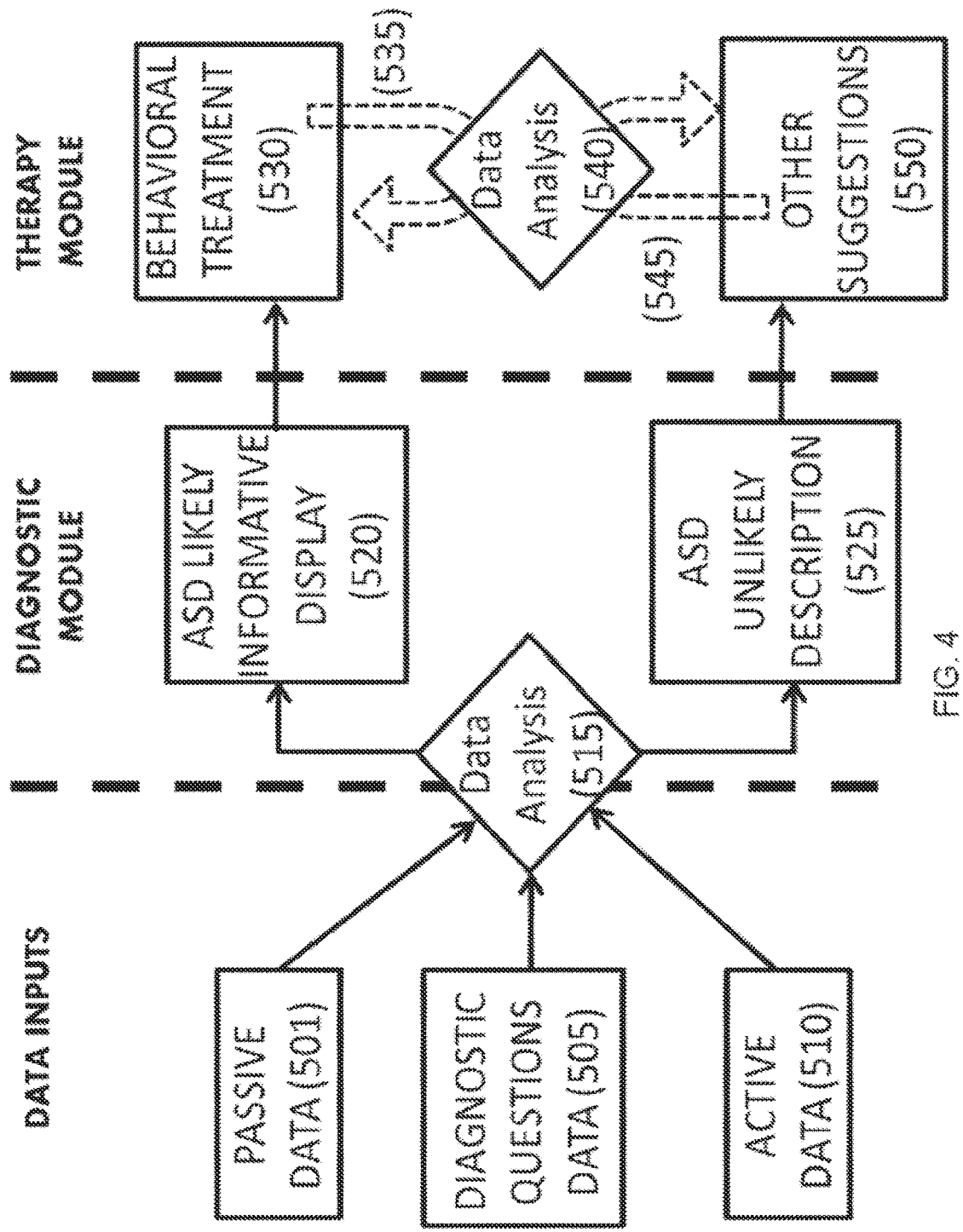
FIG. 4 illustrates an overall of data processing flows for a digital personalized medical system comprising a diagnostic module and a therapeutic module, configured to integrate information from multiple sources.

FIG. 4 illustrates an overall of data processing flows for a digital personalized medical system comprising a diagnostic module and a therapeutic module, configured to integrate information from multiple sources. Data can include passive data sources (501), passive data can be configured to provide more fine grained information, and can comprise data sets taken over longer periods of time under more nature conditions. Passive data sources can including for example, data collected from wearable devices, data collected from video feed (e.g. video feed collected from a video-enable toy, a mobile device, eye tracking data from video footage, information on the dexterity of a subject based on information gathered from three-axis sensors or gyroscopes (e.g. sensors embedded in toys or other devices that the patient may interact with for example at home, or under normal conditions outside of a medical setting), smart devices that measure any single or combination of the following: subject's speech patterns, motions, touch response time, prosody, lexical analysis, facial expressions, and other characteristic expressed by the subject. Passive data can comprise data on the motion or motions of the user, and can include subtle information that may or may not be readily detectable to an untrained individual. In some instances, passive data can provide information that can be more encompassing.

Passively collected data can comprise data collected continuously from a variety of environments. Passively collected data can provide a more complete picture of the subject and thus can improve the quality of an assessment. In some instances, for example, passively collected data can include data collected both inside and outside of a medical setting. Passively collected data taken in a medical setting can differ from passively collected data taken from outside a medical setting. Therefore, continuously collected passive data can comprise a more complete picture of a subject's general behavior and mannerisms, and thus can include data or information that a medical practitioner would not otherwise have access to. For example, a subject undergoing evaluation in a medical setting may display symptoms, gestures, or features that are representative of the subject's response to the medical environment, and thus may not provide a complete and accurate picture of the subject's behavior outside of the medical environment under more familiar conditions. The relative importance of one or more features (e.g. features assessed by a diagnostic module) derived from an assessment in the medical environment, may differ from the relative importance of one or more features derived from or assessed outside the clinical setting.

Data can comprise information collected through diagnostic tests, diagnostic questions, or questionnaires (505). In some instances, data from diagnostic tests (505) can comprise data collected from a secondary observer (e.g. a parent, guardian, or individual that is not the subject being analyzed). Data can include active data sources (510), for example data collected from devices configured for tracking eye movement, or measuring or analyzing speech patterns.

As illustrated in FIG. 4, data inputs can be fed into a diagnostic module which can comprising data analysis (515) using for example a classifier, algorithm (e.g. machine learning algorithm), or statistical model, to make a diagnosis of whether the subject is likely to have a tested disorder (e.g. Autism Spectrum Disorder) (520) or is unlikely to have the tested disorder (525). In instances where the subject is likely to have the disorder (520), a secondary party (e.g. medical practitioner, parent, guardian or other individual) may be presented with an informative display. An informative display can provide symptoms of the disorder that can be displayed as a graph depicting covariance of symptoms displayed by the subject and symptoms displayed by the average population. A list of characteristics associated with a particular diagnosis can be displayed with confidence values, correlation coefficients, or other means for displaying the relationship between a subject's performance and the average population or a population comprised of those with a similar disorders.

If the digital personalized medicine system predicts that the user is likely to have a diagnosable condition (e.g. Autism Spectrum Disorder), then a therapy module can provide a behavioral treatment (530) which can comprise behavioral interventions; prescribed activities or trainings; interventions with medical devices or other therapeutics for specific durations or, at specific times or instances. As the subject undergoes the therapy, data (e.g. passive data and diagnostic question data) can continue to be collected to perform follow-up assessments, to determine for example, whether the therapy is working. Collected data can undergo data analysis (540) (e.g. analysis using machine learning, statistical modeling, classification tasks, predictive algorithms) to make determinations about the suitability of a given subject. A growth curve display can be used to show the subject's progress against a baseline (e.g. against an age-matched cohort). Performance or progress of the individual may be measured to track compliance for the subject with a suggested behavioral therapy predicted by the therapy module may be presented as a historic and predicted performance on a growth curve. Procedures for assessing the performance of an individual subject may be repeated or iterated (535) until an appropriate behavioral treatment is identified.

The digital therapeutics treatment methods and apparatus described with reference to FIGS. 1-4 are particularly well suited for combination with the methods and apparatus to evaluate subjects with fewer questions described herein with reference to FIGS. 5A to 14. For example the components of diagnosis module 132 as described herein can be configured to assess the subject with the decreased set of questions comprising the most relevant question as described herein, and subsequently evaluated with the therapy module 134 to subsequently assess the subject with subsequent set of questions comprising the most relevant questions for monitoring treatment as described herein.

Figure 5A:
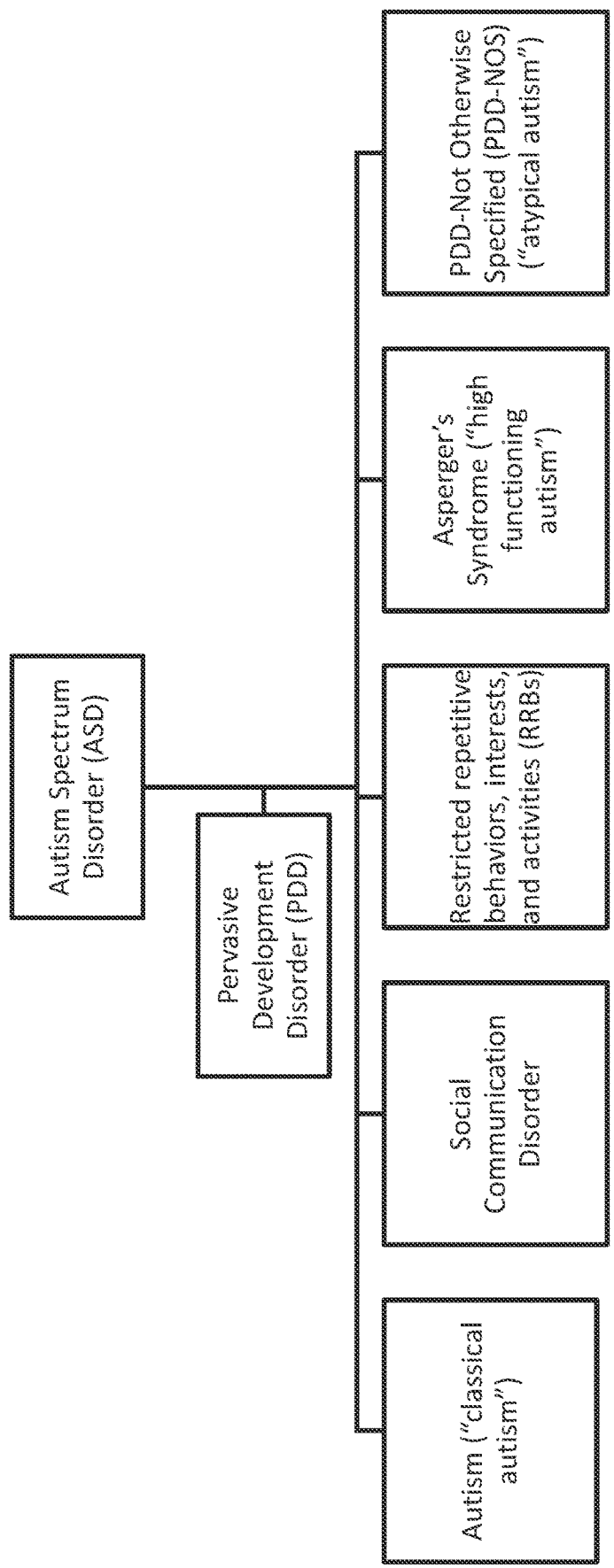
FIGS. 5A and 5B show some exemplary developmental disorders that may be diagnosed and treated using the method for diagnosis and therapy as described herein.
Figure 5B:
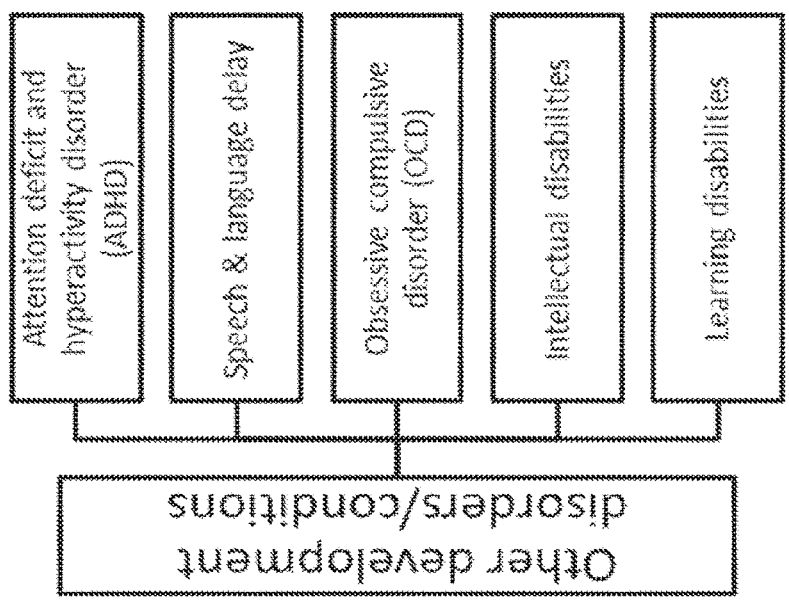

FIGS. 5A and 5B show some exemplary behavioral, neurological or mental health disorders that may be diagnosed and treated using the method for diagnosis and therapy as described herein. The diagnostic tests can be configured to evaluate a subject's risk for having one or more behavioral, neurological or mental health disorders, such as two or more related behavioral, neurological or mental health disorders. The behavioral, neurological or mental health disorders may have at least some overlap in symptoms or features of the subject. Such behavioral, neurological or mental health disorders may include pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit and hyperactivity disorder (ADHD), speech and language delay, obsessive compulsive disorder (OCD), intellectual disability, learning disability, or any other relevant development disorder, such as disorders defined in any edition of the Diagnostic and Statistical Manual of Mental Disorders (DSM). The diagnostic tests may be configured to determine the risk of the subject for having each of a plurality of disorders. The diagnostic tests may be configured to determine the subject as at greater risk of a first disorder or a second disorder of the plurality of disorders. The diagnostic tests may be configured to determine the subject as at risk of a first disorder and a second disorder with comorbidity. The diagnostic tests may be configured to predict a subject to have normal development, or have low risk of having any of the disorders the procedure is configured to screen for. The diagnostic tests may further be configured to have high sensitivity and specificity to distinguish among different severity ratings for a disorder; for example, the procedure may be configured to predict a subject's risk for having level 1 ASD, level 2 ASD, or level 3 ASD as defined in the fifth edition of the DSM (DSM-V).

Many behavioral, neurological or mental health disorders may have similar or overlapping symptoms, thus complicating the assessment of a subject's developmental disorder. The diagnostic tests described herein can be configured to evaluate a plurality of features of the subject that may be relevant to one or more behavioral, neurological or mental health disorders. The procedure can comprise an assessment model that has been trained using a large set of clinically validated data to learn the statistical relationship between a feature of a subject and clinical diagnosis of one or more behavioral, neurological or mental health disorders. Thus, as a subject participates in the diagnostic tests, the subject's feature value for each evaluated feature (e.g., subject's answer to a question) can be queried against the assessment model to identify the statistical correlation, if any, of the subject's feature value to one or more screened behavioral, neurological or mental health disorders. Based on the feature values provided by the subject, and the relationship between those values and the predicted risk for one or more behavioral, neurological or mental health disorders as determined by the assessment model, the diagnostic tests can dynamically adjust the selection of next features to be evaluated in the subject. The selection of the next feature to be evaluated may comprise an identification of the next most predictive feature, based on the determination of the subject as at risk for a particular disorder of the plurality of disorders being screened. For example, if after the subject has answered the first five questions of the diagnostic tests, the assessment model predicts a low risk of autism and a relatively higher risk of ADHD in the subject, the diagnostic tests may select features with higher relevance to ADHD to be evaluated next in the subject (e.g., questions whose answers are highly correlated with a clinical diagnosis of ADHD may be presented next to the subject). Thus, the diagnostic tests described herein can be dynamically tailored to a particular subject's risk profile, and enable the evaluation of the subject's disorder with a high level of granularity.

Figure 6:
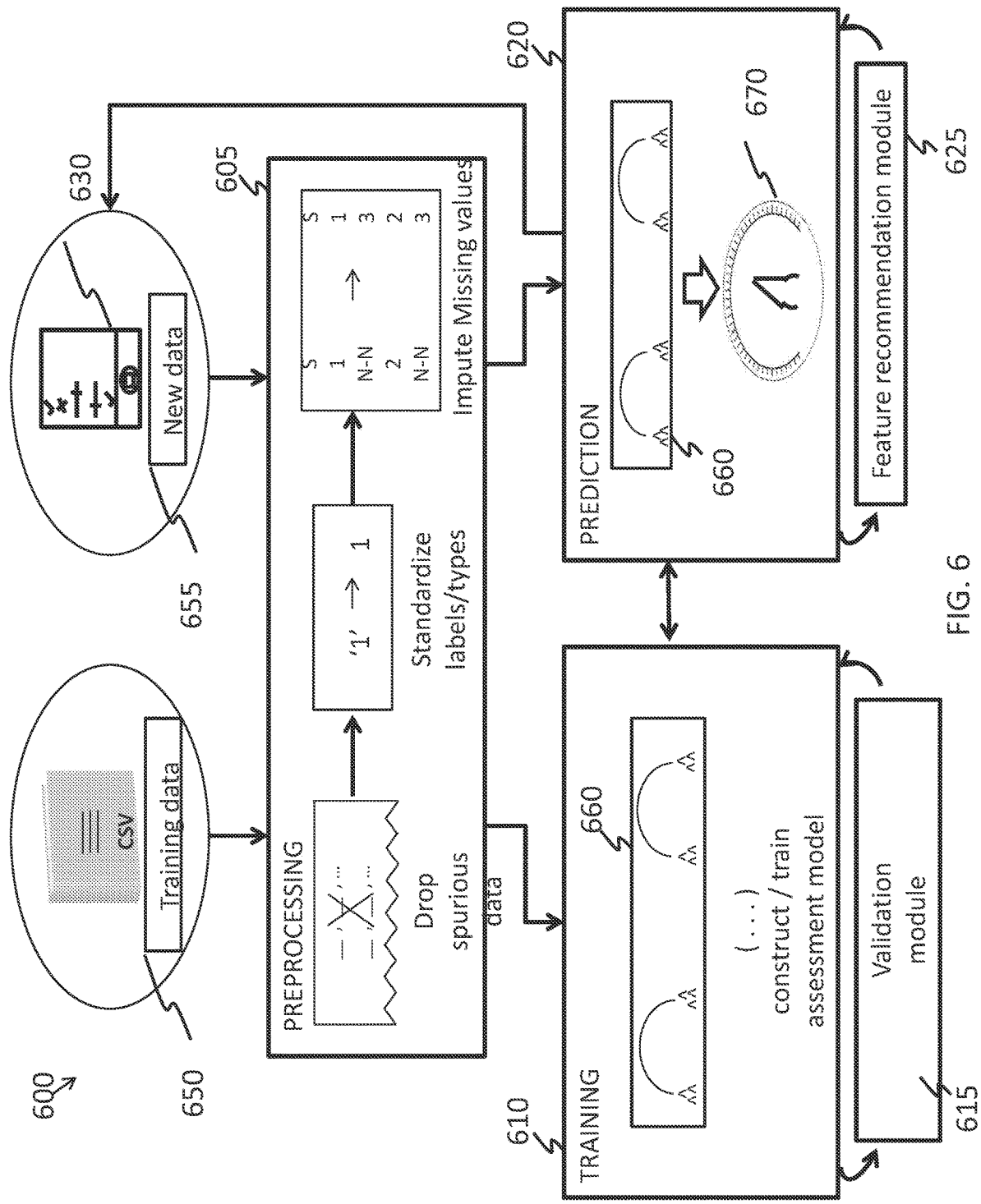
FIG. 6 is a schematic diagram of an exemplary data processing module for providing the diagnostic tests as described herein.

FIG. 6 is a schematic diagram of an exemplary data processing module 600 for providing an assessment procedure for screening a subject for cognitive function as described herein, which may comprise one or more of a plurality of behavioral, neurological or mental health disorders or conditions. The assessment procedure can evaluate a plurality of features or characteristics of the subject related to cognitive function, wherein each feature can be related to the likelihood of the subject having at least one of the plurality of behavioral, neurological or mental health disorders screenable by the procedure, for example. The assessment procedure can be administered to a subject or a caretaker of the subject with a user interface provided by a computing device. In some examples, the assessment procedure may take less than 60 minutes, 45 minutes, 30 minutes, 20 minutes, 10 minutes or less to administer to the subject. In some examples, the data processing module 600 can be at least a part of the diagnosis module as described herein. The data processing module 600 generally comprises a preprocessing module 605, a training module 610, and a prediction module 620. The data processing module can extract training data 650 from a database, or intake new data 655 with a user interface 630. The preprocessing module can apply one or more transformations to standardize the training data or new data for the training module or the prediction module. The preprocessed training data can be passed to the training module, which can construct an assessment model 660 based on the training data. The training module may further comprise a validation module 615, configured to validate the trained assessment model using any appropriate validation algorithm (e.g., Stratified K-fold cross-validation). The preprocessed new data can be passed on to the prediction module, which may output a prediction 670 of the subject's developmental disorder by fitting the new data to the assessment model constructed in the training module. The prediction module may further comprise a feature recommendation module 625, configured to select or recommend the next feature to be evaluated in the subject, based on previously provided feature values for the subject.

The training data 650, used by the training module to construct the assessment model, can comprise a plurality of datasets from a plurality of subjects, each subject's dataset comprising an array of features and corresponding feature values, and a classification of the subject's developmental disorder or condition. As described herein, the features may be evaluated in the subject via one or more of questions asked to the subject, observations of the subject, or structured interactions with the subject. Feature values may comprise one or more of answers to the questions, observations of the subject such as characterizations based on video images, or responses of the subject to a structured interaction, for example. Each feature may be relevant to the identification of one or more behavioral, neurological or mental health disorders or conditions, and each corresponding feature value may indicate the degree of presence of the feature in the specific subject. For example, a feature may be the ability of the subject to engage in imaginative or pretend play, and the feature value for a particular subject may be a score of either 0, 1, 2, 3, or 8, wherein each score corresponds to the degree of presence of the feature in the subject (e.g., 0=variety of pretend play; 1=some pretend play; 2=occasional pretending or highly repetitive pretend play; 3=no pretend play; 8=not applicable). The feature may be evaluated in the subject by way of a question presented to the subject or a caretaker such as a parent, wherein the answer to the question comprises the feature value. Alternatively or in combination, the feature may be observed in the subject, for example with a video of the subject engaging in a certain behavior, and the feature value may be identified through the observation. In addition to the array of features and corresponding feature values, each subject's dataset in the training data also comprises a classification of the subject. For example, the classification may be autism, autism spectrum disorder (ASD), or non-spectrum. Preferably, the classification comprises a clinical diagnosis, assigned by qualified personnel such as licensed clinical psychologists, in order to improve the predictive accuracy of the generated assessment model. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 605 can be configured to apply one or more transformations to the extracted training data to clean and normalize the data, for example. The preprocessing module can be configured to discard features which contain spurious metadata or contain very few observations. The preprocessing module can be further configured to standardize the encoding of feature values. Different datasets may often have the same feature value encoded in different ways, depending on the source of the dataset. For example, '900', '900.0', '904', '904.0', '−1', '−1.0', 'None', and 'NAN' may all encode for a "missing" feature value. The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model. For example, for a categorical feature wherein the corresponding feature values are encoded as integers from 1 to 9, each integer value may have a different semantic content that is independent of the other values. For example, a value of '1' and a value of '9' may both be highly correlated with a specific classification, while a value of '5' is not. The original data representation of the feature value, wherein the feature value is encoded as the integer itself, may not be able to capture the unique semantic content of each value, since the values are represented in a linear model (e.g., an answer of '5' would place the subject squarely between a '1' and a '9' when the feature is considered in isolation; however, such an interpretation would be incorrect in the aforementioned case wherein a '1' and a '9' are highly correlated with a given classification while a '5' is not). To ensure that the semantic content of each feature value is captured in the construction of the assessment model, the preprocessing module may comprise instructions to re-encode certain feature values, such as feature values corresponding to categorical features, in a "one-hot" fashion, for example. In a "one-hot" representation, a feature value may be represented as an array of bits having a value of 0 or 1, the number of bits corresponding to the number of possible values for the feature. Only the feature value for the subject may be represented as a "1", with all other values represented as a "0". For example, if a subject answered "4" to a question whose possible answers comprise integers from 1 to 9, the original data representation may be [4], and the one-hot representation may be [0 0 0 1 0 0 0 0 0]. Such a one-hot representation of feature values can allow every value to be considered independently of the other possible values, in cases where such a representation would be necessary. By thus re-encoding the training data using the most appropriate data representation for each feature, the preprocessing module can improve the accuracy of the assessment model constructed using the training data.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module. For features having categorical feature values (e.g., extent of display of a certain behavior in the subject), missing values can be provided as appropriate data representations specifically designated as such. For example, if the categorical features are encoded in a one-hot representation as described herein, the preprocessing module may encode a missing categorical feature value as an array of '0' bits. For features having continuous feature values (e.g., age of the subject), the mean of all of the possible values can be provided in place of the missing value (e.g., age of 4 years).

The training module 610 can utilize a machine learning algorithm or other algorithm to construct and train an assessment model to be used in the diagnostic tests, for example. An assessment model can be constructed to capture, based on the training data, the statistical relationship, if any, between a given feature value and a specific developmental disorder to be screened by the diagnostic tests. The assessment model may, for example, comprise the statistical correlations between a plurality of clinical characteristics and clinical diagnoses of one or more behavioral, neurological or mental health disorders. A given feature value may have a different predictive utility for classifying each of the plurality of behavioral, neurological or mental health disorders to be evaluated in the diagnostic tests. For example, in the aforementioned example of a feature comprising the ability of the subject to engage in imaginative or pretend play, the feature value of "3" or "no variety of pretend play" may have a high predictive utility for classifying autism, while the same feature value may have low predictive utility for classifying ADHD. Accordingly, for each feature value, a probability distribution may be extracted that describes the probability of the specific feature value for predicting each of the plurality of behavioral, neurological or mental health disorders to be screened by the diagnostic tests. The machine learning algorithm can be used to extract these statistical relationships from the training data and build an assessment model that can yield an accurate prediction of a developmental disorder when a dataset comprising one or more feature values is fitted to the model.

One or more machine learning algorithms may be used to construct the assessment model, such as support vector machines that deploy stepwise backwards feature selection and/or graphical models, both of which can have advantages of inferring interactions between features. For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once an assessment model is derived from the training data, the model may be used as a prediction tool to assess the risk of a subject for having one or more behavioral, neurological or mental health disorders. Machine learning analyses may be performed using one or more of many programming languages and platforms known in the art, such as R, Weka, Python, and/or Matlab, for example.

A Random Forest classifier, which generally comprises a plurality of decision trees wherein the output prediction is the mode of the predicted classifications of the individual trees, can be helpful in reducing overfitting to training data. An ensemble of decision trees can be constructed using a random subset of features at each split or decision node. The Gini criterion may be employed to choose the best partition, wherein decision nodes having the lowest calculated Gini impurity index are selected. At prediction time, a "vote" can be taken over all of the decision trees, and the majority vote (or mode of the predicted classifications) can be output as the predicted classification.

Figure 7:
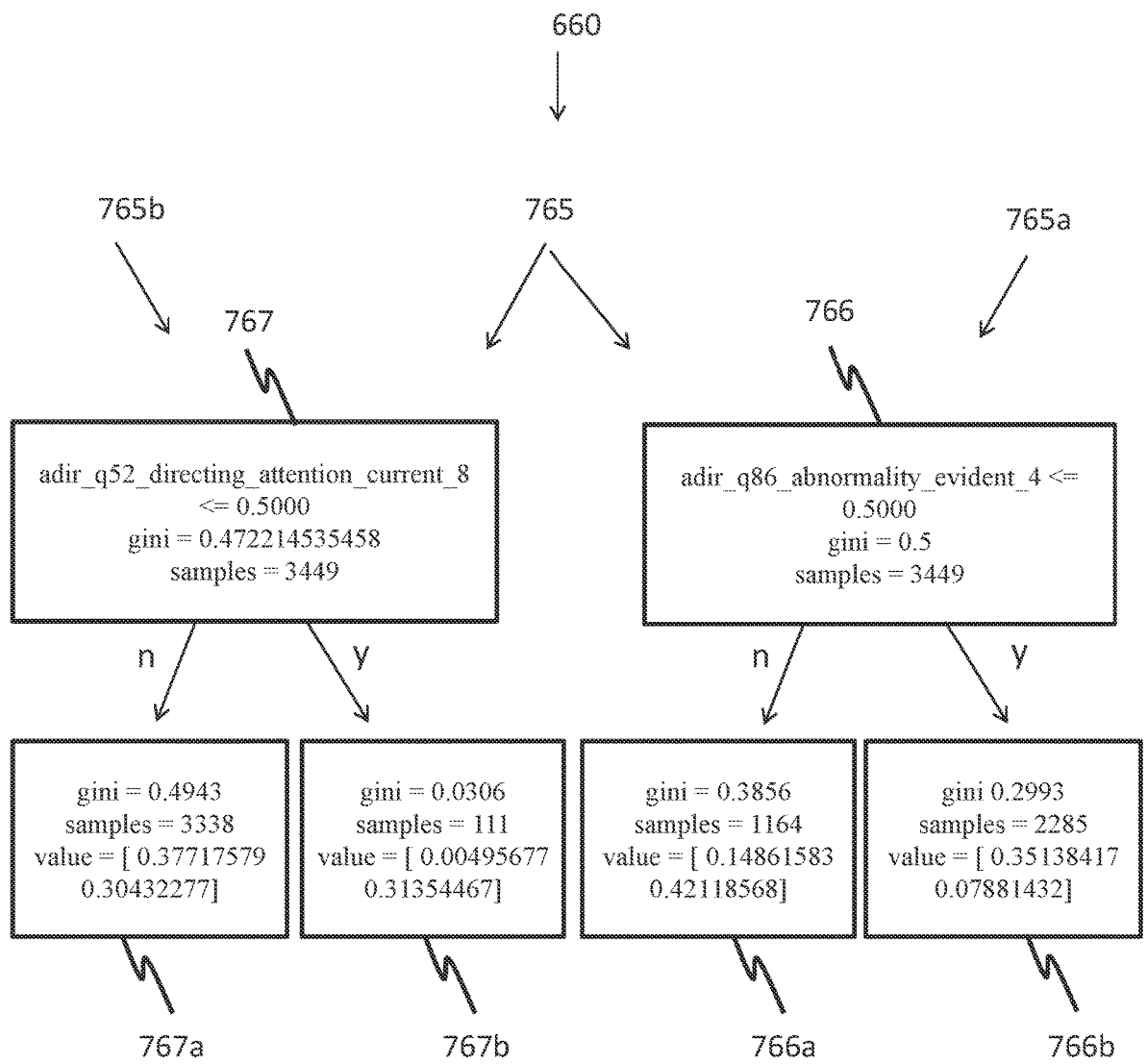
FIG. 7 is a schematic diagram illustrating a portion of an exemplary assessment model based on a Random Forest classifier.

FIG. 7 is a schematic diagram illustrating a portion of an exemplary assessment model 660 based on a Random Forest classifier. The assessment module may comprise a plurality of individual decision trees 765, such as decision trees 765a and 765b, each of which can be generated independently using a random subset of features in the training data. Each decision tree may comprise one or more decision nodes such as decision nodes 766 and 767 shown in FIG. 7, wherein each decision node specifies a predicate condition. For example, decision node 766 predicates the condition that, for a given dataset of an individual, the answer to ADI-R question #86 (age when abnormality is first evident) is 4 or less. Decision node 767 predicates the condition that, for the given dataset, the answer to ADI-R question #52 (showing and direction attention) is 8 or less. At each decision node, a decision tree can be split based on whether the predicate condition attached to the decision node holds true, leading to prediction nodes (e.g., 766a, 766b, 767a, 767b). Each prediction node can comprise output values ('value' in FIG. 7) that represent "votes" for one or more of the classifications or conditions being evaluated by the assessment model. For example, in the prediction nodes shown in FIG. 7, the output values comprise votes for the individual being classified as having autism or being non-spectrum. A prediction node can lead to one or more additional decision nodes downstream (not shown in FIG. 7), each decision node leading to an additional split in the decision tree associated with corresponding prediction nodes having corresponding output values. The Gini impurity can be used as a criterion to find informative features based on which the splits in each decision tree may be constructed.

When the dataset being queried in the assessment model reaches a "leaf", or a final prediction node with no further downstream splits, the output values of the leaf can be output as the votes for the particular decision tree. Since the Random Forest model comprises a plurality of decision trees, the final votes across all trees in the forest can be summed to yield the final votes and the corresponding classification of the subject. While only two decision trees are shown in FIG. 7, the model can comprise any number of decision trees. A large number of decision trees can help reduce overfitting of the assessment model to the training data, by reducing the variance of each individual decision tree. For example, the assessment model can comprise at least about 10 decision trees, for example at least about 100 individual decision trees or more.

An ensemble of linear classifiers may also be suitable for the derivation of an assessment model as described herein. Each linear classifier can be individually trained with a stochastic gradient descent, without an "intercept term". The lack of an intercept term can prevent the classifier from deriving any significance from missing feature values. For example, if a subject did not answer a question such that the feature value corresponding to said question is represented as an array of '0' bits in the subject's data set, the linear classifier trained without an intercept term will not attribute any significance to the array of '0' bits. The resultant assessment model can thereby avoid establishing a correlation between the selection of features or questions that have been answered by the subject and the final classification of the subject as determined by the model. Such an algorithm can help ensure that only the subject-provided feature values or answers, rather than the features or questions, are factored into the final classification of the subject.

The training module may comprise feature selection. One or more feature selection algorithms (such as support vector machine, convolutional neural nets) may be used to select features able to differentiate between individuals with and without certain behavioral, neurological or mental health disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific developmental disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data. To reduce sample bias in constructing an assessment model using skewed training data, sample weighting may be applied in training the assessment model. Sample weighting can comprise lending a relatively greater degree of significance to a specific set of samples during the model training process. For example, during model training, if the training data is skewed towards individuals diagnosed with autism, higher significance can be attributed to the data from individuals not diagnosed with autism (e.g., up to 50 times more significance than data from individuals diagnosed with autism). Such a sample weighting technique can substantially balance the sample bias present in the training data, thereby producing an assessment model with reduced bias and improved accuracy in classifying data in the real world. To further reduce the contribution of training data sample bias to the generation of an assessment model, a boosting technique may be implemented during the training process. Boosting comprises an iterative process, wherein after one iteration of training, the weighting of each sample data point is updated. For example, samples that are misclassified after the iteration can be updated with higher significances. The training process may then be repeated with the updated weightings for the training data.

The training module may further comprise a validation module 615 configured to validate the assessment model constructed using the training data. For example, a validation module may be configured to implement a Stratified K-fold cross validation, wherein k represents the number of partitions that the training data is split into for cross validation. For example, k can be any integer greater than 1, such as 3, 4, 5, 6, 7, 8, 9, or 10, or possibly higher depending on risk of overfitting the assessment model to the training data.

The training module may be configured to save a trained assessment model to a local memory and/or a remote server, such that the model can be retrieved for modification by the training module or for the generation of a prediction by the prediction module 620.

Figure 8:
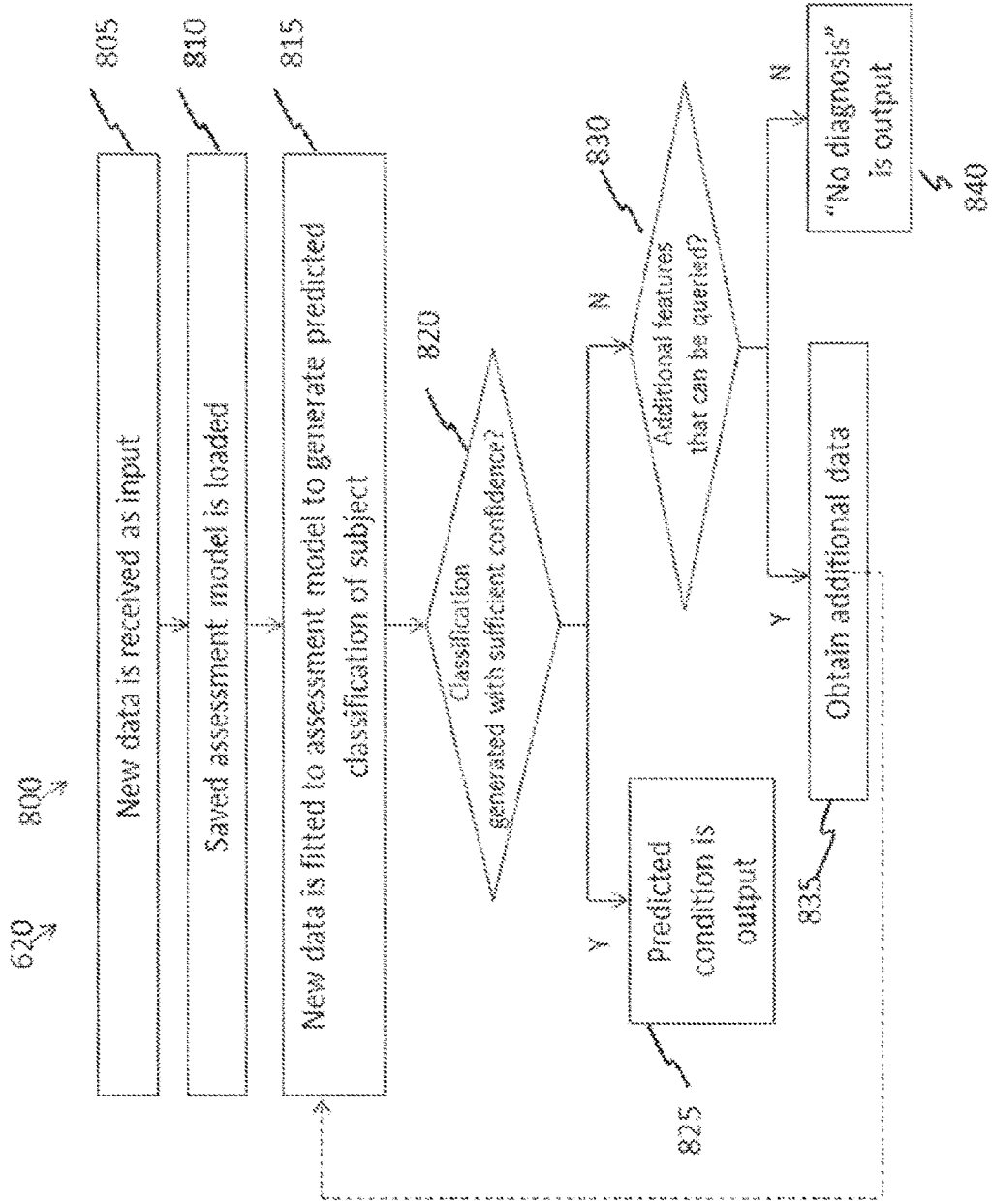
FIG. 8 is an exemplary operational flow of a prediction module as described herein.

FIG. 8 is an exemplary operational flow 800 of a method of a prediction module 620 as described herein. The prediction module 620 can be configured to generate a predicted classification (e.g., developmental disorder) of a given subject, by fitting new data to an assessment model constructed in the training module. At step 805, the prediction module can receive new data that may have been processed by the preprocessing module to standardize the data, for example by dropping spurious metadata, applying uniform encoding of feature values, re-encoding select features using different data representations, and/or imputing missing data points, as described herein. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The new data provided to the prediction module may or may not have a known classification or diagnosis associated with the data; either way, the prediction module may not use any pre-assigned classification information in generating the predicted classification for the subject. The new data may comprise a previously-collected, complete dataset for a subject to be diagnosed or assessed for the risk of having one or more of a plurality of behavioral, neurological or mental health disorders. Alternatively or in combination, the new data may comprise data collected in real time from the subject or a caretaker of the subject, for example with a user interface as described in further detail herein, such that the complete dataset can be populated in real time as each new feature value provided by the subject is sequentially queried against the assessment model.

At step 810, the prediction module can load a previously saved assessment model, constructed by the training module, from a local memory and/or a remote server configured to store the model. At step 815, the new data is fitted to the assessment model to generate a predicted classification of the subject. At step 820, the module can check whether the fitting of the data can generate a prediction of one or more specific disorders (e.g., autism, ADHD, etc.) within a confidence interval exceeding a threshold value, for example within a 90% or higher confidence interval, for example 95% or more. If so, as shown in step 825, the prediction module can output the one or more behavioral, neurological or mental health disorders as diagnoses of the subject or as disorders for which the subject is at risk. The prediction module may output a plurality of behavioral, neurological or mental health disorders for which the subject is determined to at risk beyond the set threshold, optionally presenting the plurality of disorders in order of risk. The prediction module may output one developmental disorder for which the subject is determined to be at greatest risk. The prediction module may output two or more development disorders for which the subject is determined to risk with comorbidity. The prediction module may output determined risk for each of the one or more behavioral, neurological or mental health disorders in the assessment model. If the prediction module cannot fit the data to any specific developmental disorder within a confidence interval at or exceeding the designated threshold value, the prediction module may determine, in step 830, whether there are any additional features that can be queried. If the new data comprises a previously-collected, complete dataset, and the subject cannot be queried for any additional feature values, "no diagnosis" may be output as the predicted classification, as shown in step 840. If the new data comprises data collected in real time from the subject or caretaker during the prediction process, such that the dataset is updated with each new input data value provided to the prediction module and each updated dataset is fitted to the assessment model, the prediction module may be able to query the subject for additional feature values. If the prediction module has already obtained data for all features included in the assessment module, the prediction module may output "no diagnosis" as the predicted classification of the subject, as shown in step 840. If there are features that have not yet been presented to the subject, as shown in step 835, the prediction module may obtain additional input data values from the subject, for example by presenting additional questions to the subject. The updated dataset including the additional input data may then be fitted to the assessment model again (step 815), and the loop may continue until the prediction module can generate an output.

Figure 9:
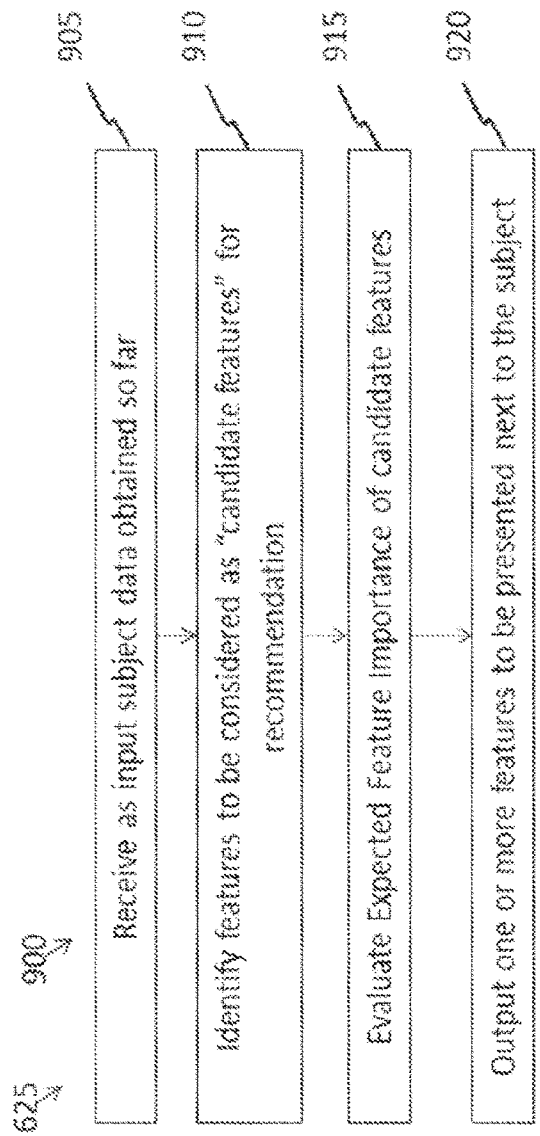
FIG. 9 is an exemplary operational flow of a feature recommendation module as described herein.

FIG. 9 is an exemplary operational flow 900 of a feature recommendation module 625 as described herein by way of a non-limiting example. The prediction module may comprise a feature recommendation module 625, configured to identify, select or recommend the next most predictive or relevant feature to be evaluated in the subject, based on previously provided feature values for the subject. For example, the feature recommendation module can be a question recommendation module, wherein the module can select the most predictive next question to be presented to a subject or caretaker, based on the answers to previously presented questions. The feature recommendation module can be configured to recommend one or more next questions or features having the highest predictive utility in classifying a particular subject's developmental disorder. The feature recommendation module can thus help to dynamically tailor the assessment procedure to the subject, so as to enable the prediction module to produce a prediction with a reduced length of assessment and improved sensitivity and accuracy. Further, the feature recommendation module can help improve the specificity of the final prediction generated by the prediction module, by selecting features to be presented to the subject that are most relevant in predicting one or more specific behavioral, neurological or mental health disorders that the particular subject is most likely to have, based on feature values previously provided by the subject.

At step 905, the feature recommendation module can receive as input the data already obtained from the subject in the assessment procedure. The input subject data can comprise an array of features and corresponding feature values provided by the subject. At step 910, the feature recommendation module can select one or more features to be considered as "candidate features" for recommendation as the next feature(s) to be presented to one or more of the subject, caretaker or clinician. Features that have already been presented can be excluded from the group of candidate features to be considered. Optionally, additional features meeting certain criteria may also be excluded from the group of candidate features, as described in further detail herein.

At step 915, the feature recommendation module can evaluate the "expected feature importance" of each candidate feature. The candidate features can be evaluated for their "expected feature importance", or the estimated utility of each candidate feature in predicting a specific developmental disorder for the specific subject. The feature recommendation module may utilize an algorithm based on: (1) the importance or relevance of a specific feature value in predicting a specific developmental disorder; and (2) the probability that the subject may provide the specific feature value. For example, if the answer of "3" to ADOS question B5 is highly correlated with a classification of autism, this answer can be considered a feature value having high utility for predicting autism. If the subject at hand also has a high probability of answering "3" to said question B5, the feature recommendation module can determine this question to have high expected feature importance. An algorithm that can be used to determine the expected feature importance of a feature is described in further detail in reference to FIG. 10, for example.

At step 920, the feature recommendation module can select one or more candidate features to be presented next to the subject, based on the expected feature importance of the features as determined in step 915. For example, the expected feature importance of each candidate feature may be represented as a score or a real number, which can then be ranked in comparison to other candidate features. The candidate feature having the desired rank, for example a top 10, top 5, top 3, top 2, or the highest rank, may be selected as the feature to the presented next to the subject.

Figure 10:
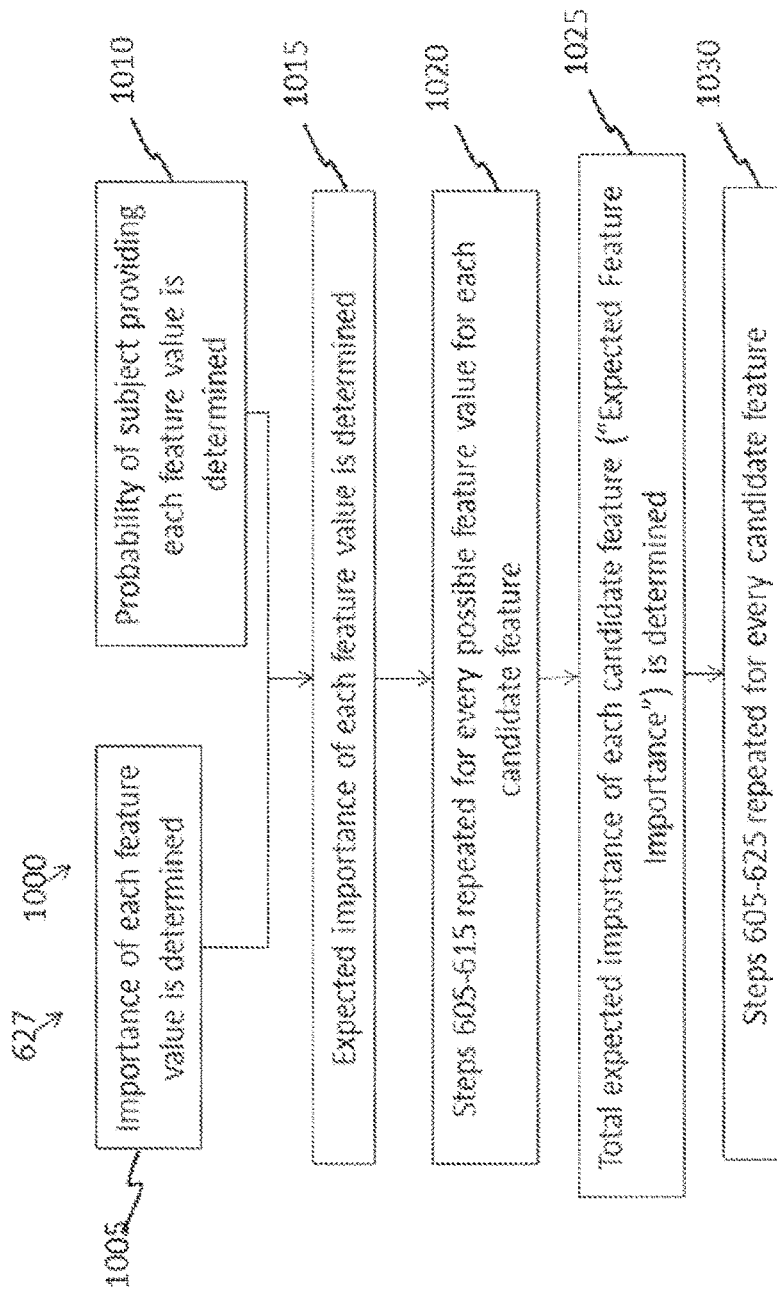
FIG. 10 is an exemplary operational flow of an expected feature importance determination algorithm as performed by a feature recommendation module described herein.

FIG. 10 is an exemplary operational flow 1000 of method of determining an expected feature importance determination algorithm 627 as performed by a feature recommendation module 625 described herein.

At step 1005, the algorithm can determine the importance or relevance of a specific feature value in predicting a specific developmental disorder. The importance or relevance of a specific feature value in predicting a specific developmental disorder can be derived from the assessment model constructed using training data. Such a "feature value importance" can be conceptualized as a measure of how relevant a given feature value's role is, should it be present or not present, in determining a subject's final classification. For example, if the assessment model comprises a Random Forest classifier, the importance of a specific feature value can be a function of where that feature is positioned in the Random Forest classifier's branches. Generally, if the average position of the feature in the decision trees is relatively high, the feature can have relatively high feature importance. The importance of a feature value given a specific assessment model can be computed efficiently, either by the feature recommendation module or by the training module, wherein the training module may pass the computed statistics to the feature recommendation module. Alternatively, the importance of a specific feature value can be a function of the actual prediction confidence that would result if said feature value was provided by the subject. For each possible feature value for a given candidate feature, the feature recommendation module can be configured to calculate the actual prediction confidence for predicting one or more behavioral, neurological or mental health disorders, based on the subject's previously provided feature values and the currently assumed feature value.

Each feature value may have a different importance for each developmental disorder for which the assessment procedure is designed to screen. Accordingly, the importance of each feature value may be represented as a probability distribution that describes the probability of the feature value yielding an accurate prediction for each of the plurality of behavioral, neurological or mental health disorders being evaluated.

At step 1010, the feature recommendation module can determine the probability of a subject providing each feature value. The probability that the subject may provide a specific feature value can be computed using any appropriate statistical model. For example, a large probabilistic graphical model can be used to find the values of expressions such as:

$$\text{prob}(E=1|A=1, B=2, C=1)$$

where A, B, and C represent different features or questions in the prediction module and the integers 1 and 2 represent different possible feature values for the feature (or possible answers to the questions). The probability of a subject providing a specific feature value may then be computed using Bayes' rule, with expressions such as:

$$\text{prob}(E=1|A=1, B=2, C=1) = \text{prob}(E=1, A=1, B=2, C=1) / \text{prob}(A=1, B=2, C=1)$$

Such expressions may be computationally expensive, in terms of both computation time and required processing resources. Alternatively or in combination with computing the probabilities explicitly using Bayes' rule, logistic regression or other statistical estimators may be used, wherein the probability is estimated using parameters derived from a machine learning algorithm. For example, the following expression may be used to estimate the probability that the subject may provide a specific feature value:

$$\text{prob}(E=1|A=1, B=2, C=1) \approx \text{sigmoid}(a1*A + a2*B + a3*C + a4),$$

wherein a1, a2, a3, and a4 are constant coefficients determined from the trained assessment model, learned using an optimization algorithm that attempts to make this expression maximally correct, and wherein sigmoid is a nonlinear function that enables this expression to be turned into a probability. Such an algorithm can be quick to train, and the resulting expressions can be computed quickly in application, e.g., during administration of the assessment procedure. Although reference is made to four coefficients, as many coefficients as are helpful may be used as will be recognized by a person of ordinary skill in the art.

At step 1015, the expected importance of each feature value can be determined based on a combination of the metrics calculated in steps 1005 and 1010. Based on these two factors, the feature recommendation module can determine the expected utility of the specific feature value in predicting a specific developmental disorder. Although reference is made herein to the determination of expected importance via multiplication, the expected importance can be determined by combining coefficients and parameters in many ways, such as with look up tables, logic, or division, for example.

At step 1020, steps 1005-1015 can be repeated for every possible feature value for each candidate feature. For example, if a particular question has 4 possible answers, the expected importance of each of the 4 possible answers is determined.

At step 1025, the total expected importance, or the expected feature importance, of each candidate feature can be determined. The expected feature importance of each feature can be determined by summing the feature value importances of every possible feature value for the feature, as determined in step 1020. By thus summing the expected utilities across all possible feature values for a given feature, the feature recommendation module can determine the total expected feature importance of the feature for predicting a specific developmental disorder in response to previous answers.

At step 1030, steps 1005-1025 can be repeated for every candidate feature being considered by the feature recommendation module. The candidate features may comprise a subset of possible features such as questions. Thus, an expected feature importance score for every candidate feature can be generated, and the candidate features can be ranked in order of highest to lowest expected feature importance.

Optionally, in addition to the two factors determined in steps 1005 and 1010, a third factor may also be taken into account in determining the importance of each feature value. Based on the subject's previously provided feature values, the subject's probability of having one or more of the plurality of behavioral, neurological or mental health disorders can be determined. Such a probability can be determined based on the probability distribution stored in the assessment model, indicating the probability of the subject having each of the plurality of screened behavioral, neurological or mental health disorders based on the feature values provided by the subject. In selecting the next feature to be presented to the subject, the algorithm may be configured to give greater weight to the feature values most important or relevant to predicting the one or more behavioral, neurological or mental health disorders that the subject at hand is most likely to have. For example, if a subject's previously provided feature values indicate that the subject has a higher probability of having either an intellectual disability or speech and language delay than any of the other behavioral, neurological or mental health disorders being evaluated, the feature recommendation module can favor feature values having high importance for predicting either intellectual disability or speech and language delay, rather than features having high importance for predicting autism, ADHD, or any other developmental disorder that the assessment is designed to screen for. The feature recommendation module can thus enable the prediction module to tailor the prediction process to the subject at hand, presenting more features that are relevant to the subject's potential developmental disorder to yield a final classification with higher granularity and confidence.

Although the above steps show an exemplary operational flow 1000 of an expected feature importance determination algorithm 627, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

An exemplary implementation of the feature recommendation module is now described. Subject X has provided answers (feature values) to questions (features) A, B, and C in the assessment procedure:

Subject $X=\{`A`:1, `B`:2, `C`:1\}$

The feature recommendation module can determine whether question D or question E should be presented next in order to maximally increase the predictive confidence with which a final classification or diagnosis can be reached. Given Subject X's previous answers, the feature recommendation module determines the probability of Subject X providing each possible answer to each of questions D and E, as follows:

$\text{prob}(E=1|A=1,B=2,C=1)=0.1$ $\text{prob}(E=2|A=1,B=2,C=1)=0.9$ $\text{prob}(D=1|A=1,B=2,C=1)=0.7$ $\text{prob}(D=2|A=1,B=2,C=1)=0.3$ The feature importance of each possible answer to each of questions D and E can be computed based on the assessment model as described. Alternatively, the feature importance of each possible answer to each of questions D and E can be computed as the actual prediction confidence that would result if the subject were to give the specific answer. The importance of each answer can be represented using a range of values on any appropriate numerical scale. For example:

$\text{importance}(E=1)=1$ $\text{importance}(E=2)=3$ $\text{importance}(D=1)=2$ $\text{importance}(D=2)=4$ Based on the computed probabilities and the feature value importances, the feature recommendation module can compute the expected feature importance of each question as follows: Expectation[importance(E)]=(prob(E=1|A=1, B=2, C=1)*importance(E=1)

$$+ (prob(E = 2 \mid A = 1, B = 2, C = 1) * \text{importance}(E = 2)$$
$$= 0.1 * 1 + 0.9 * 3$$
$$= 2.8$$

Expectation[importance(D)] =
$$(prob(D = 1 \mid A = 1, B = 2, C = 1) * \text{importance}(D = 1)$$
$$+ (prob(D = 2 \mid A = 1, B = 2, C = 1) * \text{importance}(D = 2)$$
$$= 0.7 * 2 + 0.3 * 4$$
$$= 2.6$$

Hence, the expected feature importance (also referred to as relevance) from the answer of question E is determined to be higher than that of question D, even though question D has generally higher feature importances for its answers. The feature recommendation module can therefore select question E as the next question to be presented to Subject X.

When selecting the next best feature to be presented to a subject, the feature recommendation module 625 may be further configured to exclude one or more candidate features from consideration, if the candidate features have a high co-variance with a feature that has already been presented to the subject. The co-variance of different features may be determined based on the training data, and may be stored in the assessment model constructed by the training module. If a candidate feature has a high co-variance with a previously presented feature, the candidate feature may add relatively little additional predictive utility, and may hence be omitted from future presentation to the subject in order to optimize the efficiency of the assessment procedure.

The prediction module 620 may interact with the person participating in the assessment procedure (e.g., a subject or the subject's caretaker) with a user interface 630. The user interface may be provided with a user interface, such as a display of any computing device that can enable the user to access the prediction module, such as a personal computer, a tablet, or a smartphone. The computing device may comprise a processor that comprises instructions for providing the user interface, for example in the form of a mobile application. The user interface can be configured to display instructions from the prediction module to the user, and/or receive input from the user with an input method provided by the computing device. Thus, the user can participate in the assessment procedure as described herein by interacting with the prediction module with the user interface, for example by providing answers (feature values) in response to questions (features) presented by the prediction module. The user interface may be configured to administer the assessment procedure in real-time, such that the user answers one question at a time and the prediction module can select the next best question to ask based on recommendations made by the feature recommendation module. Alternatively or in combination, the user interface may be configured to receive a complete set of new data from a user, for example by allowing a user to upload a complete set of feature values corresponding to a set of features.

As described herein, the features of interest relevant to identifying one or more behavioral, neurological or mental health disorders may be evaluated in a subject in many ways. For example, the subject or caretaker or clinician may be asked a series of questions designed to assess the extent to which the features of interest are present in the subject. The answers provided can then represent the corresponding feature values of the subject. The user interface may be configured to present a series of questions to the subject (or any person participating in the assessment procedure on behalf of the subject), which may be dynamically selected from a set of candidate questions as described herein. Such a question-and-answer based assessment procedure can be administered entirely by a machine, and can hence provide a very quick prediction of the subject's developmental disorder(s).

Alternatively or in combination, features of interest in a subject may be evaluated with observation of the subject's behaviors, for example with videos of the subject. The user interface may be configured to allow a subject or the subject's caretaker to record or upload one or more videos of the subject. The video footage may be subsequently analyzed by qualified personnel to determine the subject's feature values for features of interest. Alternatively or in combination, video analysis for the determination of feature values may be performed by a machine. For example, the video analysis may comprise detecting objects (e.g., subject, subject's spatial position, face, eyes, mouth, hands, limbs, fingers, toes, feet, etc.), followed by tracking the movement of the objects. The video analysis may infer the gender of the subject, and/or the proficiency of spoken language(s) of the subject. The video analysis may identify faces globally, or specific landmarks on the face such as the nose, eyes, lips and mouth to infer facial expressions and track these expressions over time. The video analysis may detect eyes, limbs, fingers, toes, hands, feet, and track their movements over time to infer behaviors. In some cases, the analysis may further infer the intention of the behaviors, for example, a child being upset by noise or loud music, engaging in self-harming behaviors, imitating another person's actions, etc. The sounds and/or voices recorded in the video files may also be analyzed. The analysis may infer a context of the subject's behavior. The sound/voice analysis may infer a feeling of the subject. The analysis of a video of a subject, performed by a human and/or by a machine, can yield feature values for the features of interest, which can then be encoded appropriately for input into the prediction module. A prediction of the subject's developmental disorder may then be generated based on a fitting of the subject's feature values to the assessment model constructed using training data.

Alternatively or in combination, features of interest in a subject may be evaluated through structured interactions with the subject. For example, the subject may be asked to play a game such as a computer game, and the performance of the subject on the game may be used to evaluate one or more features of the subject. The subject may be presented with one or more stimuli (e.g., visual stimuli presented to the subject via a display), and the response of the subject to the stimuli may be used to evaluate the subject's features. The subject may be asked to perform a certain task (e.g., subject may be asked to pop bubbles with his or her fingers), and the response of the subject to the request or the ability of the subject to carry out the requested task may be used to evaluate to the subject's features.

The methods and apparatus described herein can be configured in many ways to determine the next most predictive or relevant question. At least a portion of the software instructions as described herein can be configured to run locally on a local device so as to provide the user interface and present questions and receive answers to the questions. The local device can be configured with software instructions of an application program interface (API) to query a remote server for the most predictive next question. The API can return an identified question based on the feature importance as described herein, for example. Alternatively or in combination, the local processor can be configured with instructions to determine the most predictive next question in response to previous answers. For example, the prediction module 620 may comprise software instructions of a remote server, or software instructions of a local processor, and combinations thereof. Alternatively or in combination, the feature recommendation module 625 may comprise software instructions of a remote server, or software instructions of a local processor, and combinations thereof, configured to determine the most predictive next question, for example. The exemplary operational flow 1000 of method of determining an expected feature importance determination algorithm 627 as performed by a feature recommendation module 625 described herein can be performed with one or more processors as described herein, for example.

Figure 11:
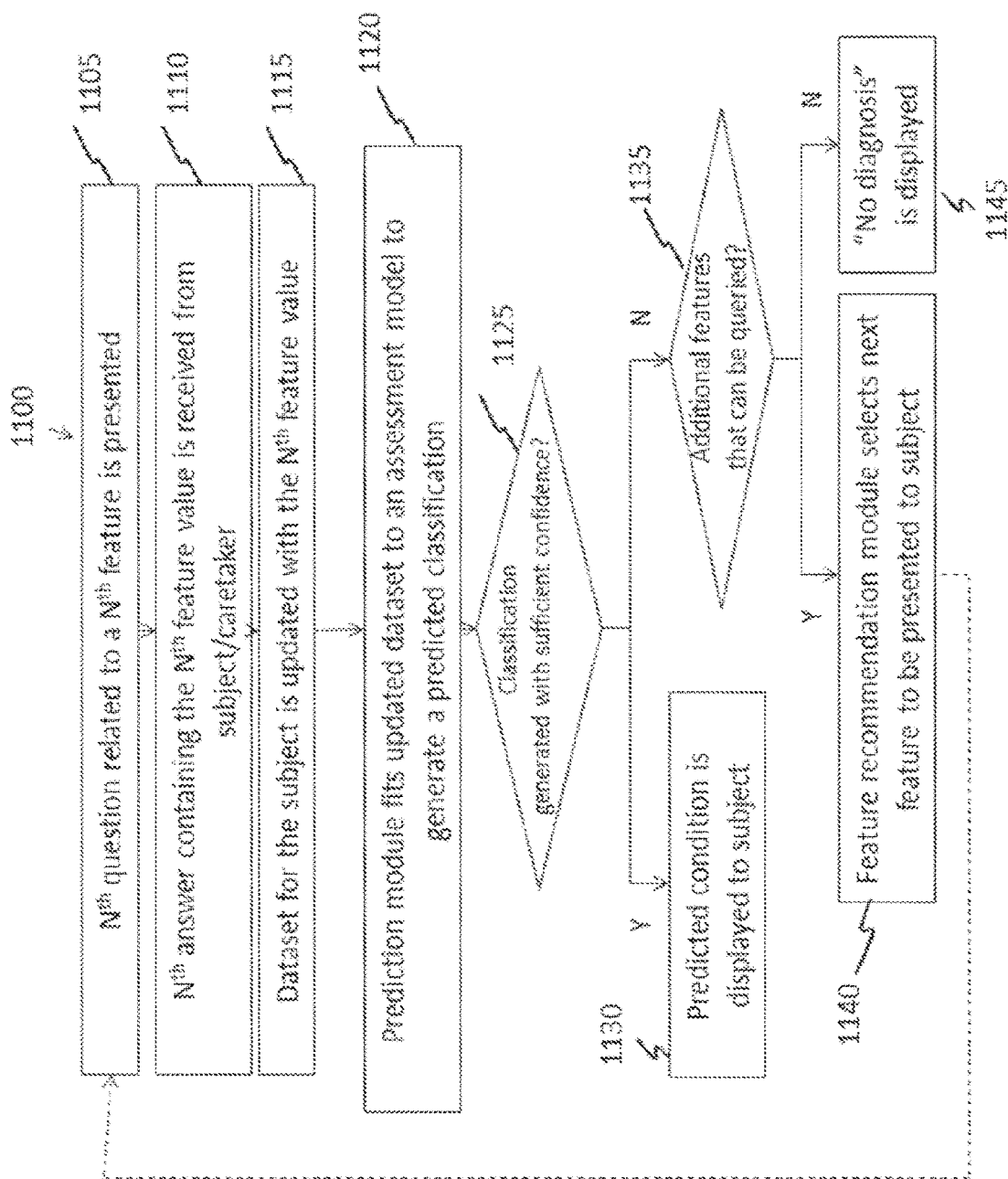
FIG. 11 illustrates a method of administering a diagnostic test as described herein.

FIG. 11 illustrates a method 1100 of administering an assessment procedure as described herein. The method 1100 may be performed with a user interface provided on a computing device, the computing device comprising a display and a user interface for receiving user input in response to the instructions provided on the display. The user participating in the assessment procedure may be the subject himself, or another person participating in the procedure on behalf of the subject, such as the subject's caretaker. At step 1105, an $N^{th}$ question related an $N^{th}$ feature can be presented to the user with the display. At step 1110, the subject's answer containing the corresponding $N^{th}$ feature value can be received. At step 1115, the dataset for the subject at hand can be updated to include $N^{th}$ the feature value provided for the subject. At step 1120, the updated dataset can be fitted to an assessment model to generate a predicted classification. Step 1120 may be performed by a prediction module, as described herein. At step 1125, a check can be performed to determine whether the fitting of the data can generate a prediction of a specific developmental disorder (e.g., autism, ADHD, etc.) sufficient confidence (e.g., within at least a 90% confidence interval). If so, as shown at step 1130, the predicted developmental disorder can be displayed to the user. If not, in step 1135, a check can be performed to determine whether there are any additional features that can be queried. If yes, as shown at step 1140, the feature recommendation module may select the next feature to be presented to the user, and steps 1105-1125 may be repeated until a final prediction (e.g., a specific developmental disorder or "no diagnosis") can be displayed to the subject. If no additional features can be presented to the subject, "no diagnosis" may be displayed to the subject, as shown at step 1145.

Although the above steps show an exemplary a method 1100 of administering an assessment procedure, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 12:
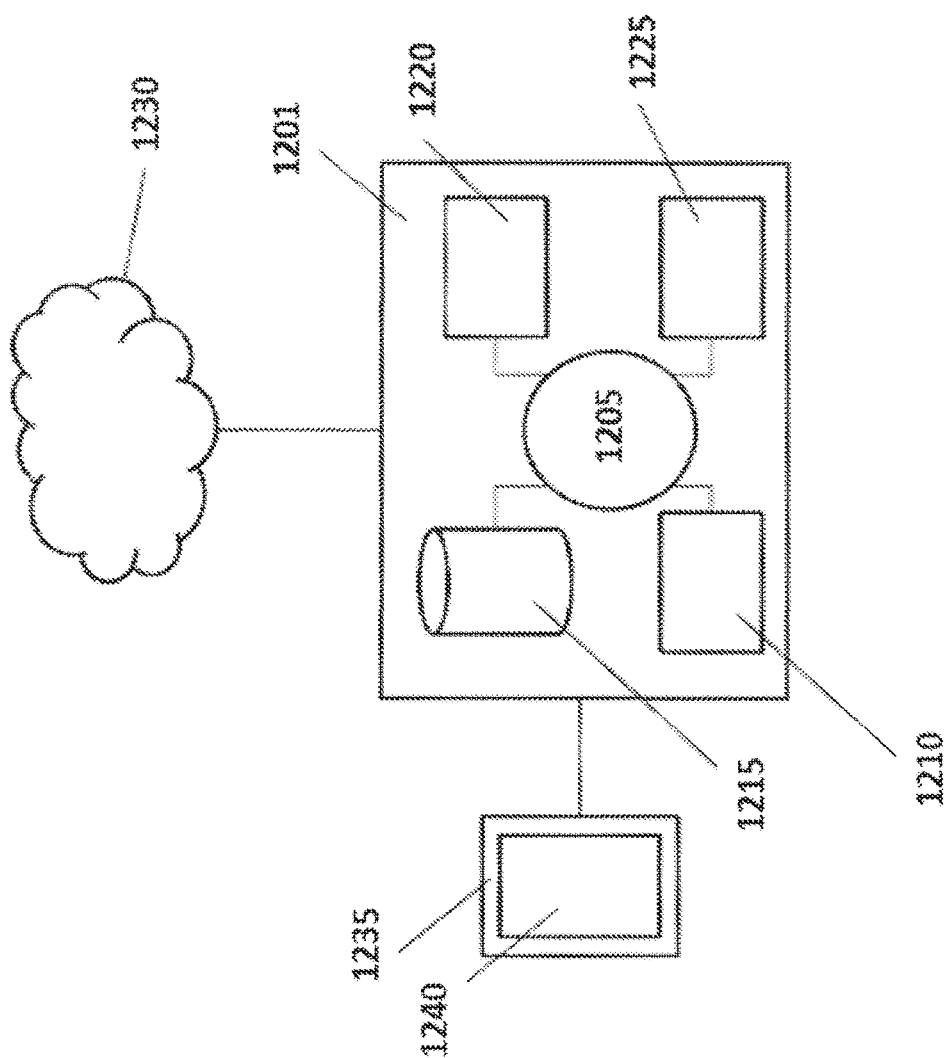
FIG. 12 shows an exemplary computer system suitable for incorporation with the methods and apparatus described herein.

The present disclosure provides computer control systems that are programmed to implement methods of the disclosure. FIG. 12 shows a computer system 1201 suitable for incorporation with the methods and apparatus described herein. The computer system 1201 can process various aspects of information of the present disclosure, such as, for example, questions and answers, responses, statistical analyses. The computer system 1201 can be an electronic device of a user or a computer system that is remotely located with respect to the electronic device. The electronic device can be a mobile electronic device.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., a parent). Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), personal digital assistants, wearable medical devices (e.g., Fitbits), or medical device monitors (e.g., seizure monitors). The user can access the computer system 1201 with the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, questions and answers, analysis results, recommendations. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the central processing unit 1205. The algorithm can be, for example, random forest, graphical models, support vector machine or other.

Although the above steps show a method of a system in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Figure 13:
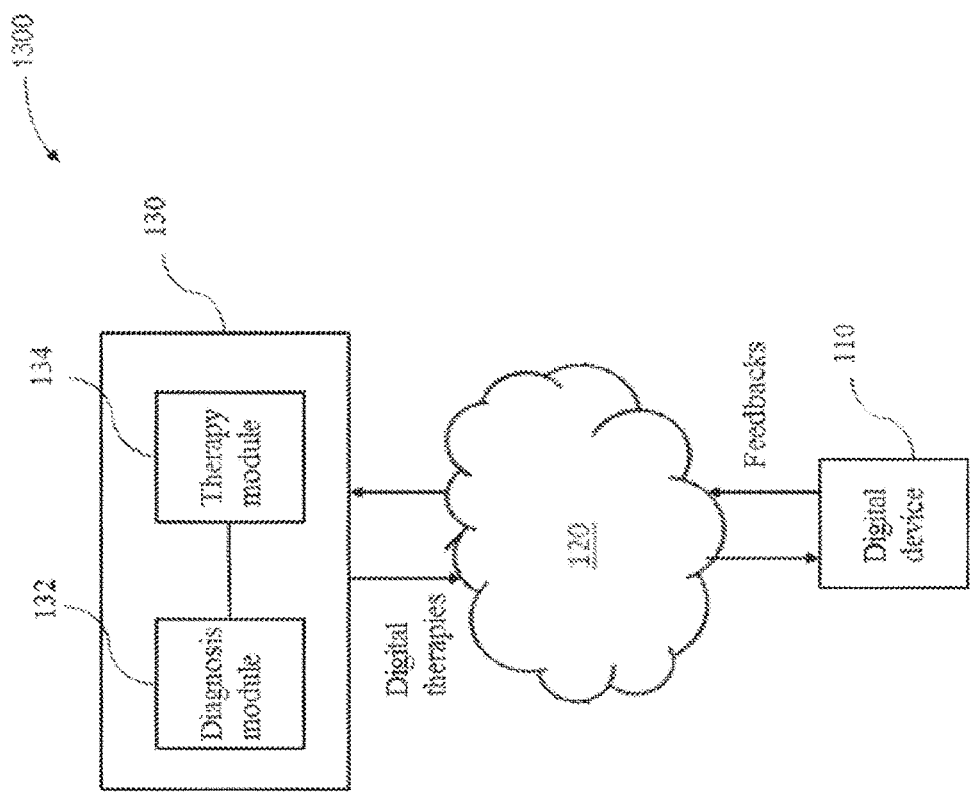
FIG. 13 illustrates an exemplary system diagram for a digital personalized medicine platform with a feedback loop and reduced tests.

FIG. 13 illustrates an exemplary system diagram for a digital personalized medicine platform 1300 with a feedback loop and reduced tests. The platform 1300 can provide diagnosis and treatment of pediatric cognitive and behavioral conditions associated with developmental delays, for example. A user digital device 110, for example a mobile device such as a smart phone, an activity monitors, or a wearable digital monitor, can records data and metadata related to a patient. Data may be collected based on interactions of the patient with the device, as well as based on interactions with caregivers and health care professionals, as discussed hereinabove.

The digital device 110 can communicate with a personalized medical system 130 over a communication network 120. The personalized medical system 130 can comprises a diagnosis module 132 to provide initial and updated diagnosis of a patient's developmental status, and a therapeutic module 134 to provide personalized therapy recommendations in response to the diagnoses of diagnosis module 132.

In some instances, the diagnosis module 132 can comprise data processing module as described herein. The data processing module can enable the diagnosis module 132 to provide an assessment on the subject with reduced number of test questions. The data processing module can comprise a preprocessing module, a training module and a prediction module as described herein. The data processing module can extract training data from a database or a user, apply one or more transformations to standardize the training data and pass the standardized training data to the training module. The training module can utilize a machine learning algorithm or other algorithm to construct and train an assessment model to be used in the diagnostic tests, based on the standardized training data. Once an assessment model is derived from the training data, the model may be used as a prediction tool to assess the risk of a subject for cognitive function such as developmental advancement, or one or more disorders such as behavioral, neurological or mental health disorders. The training data can comprise data developed on a population where the subject patient is not a member of the population. The prediction module can be configured to generate a predicted classification of cognitive function (e.g., developmental disorder) of a given subject, by fitting new data to an assessment model constructed in the training module. The data processing module can identify a most predictive next question based on a plurality of answers to a plurality of asked questions, as discussed herein, such that a person can be diagnosed or identified as at risk and treated with fewer questions.

Diagnostic tests (for example, a set of tests and questions) as generated from the diagnosis module 132 can be provided to the patient or caregiver via the digital device 110. The patient's answers to the diagnostic tests can be received by the diagnosis module 132. The diagnosis module 132 can generate an initial diagnosis based on the patient's answers. For example, the diagnostic module may diagnose autism-related speech delay based on questions asked to the caregiver and tests administered to the patient such as vocabulary or verbal communication tests.

The diagnosis module can communicate its initial diagnosis to the therapy module 134, which uses the initial diagnosis to suggest initial therapies to be performed to treat any diagnosed symptoms. The therapy module 134 sends its recommended therapies to the digital device 110, including instructions for the patient and caregivers to perform the therapies recommended over a given time frame. The patient and caregivers can provide feedback to the diagnostic module 132, and the diagnostic module 132 can then instruct the data processing module to provide new diagnostic tests and questions to the digital device 110. The diagnostic module 132 then provides an updated diagnosis to the therapy module 134 which suggests updated therapies to be performed by the patient and caregivers as a next step of therapy. Therefore, a feedback loop between the patient and caregivers, the diagnostic module and the therapy module can be formed, and the patient can be diagnosed with fewer questions. The feedback can identify relative levels of efficacy, compliance and responses resulting from the therapeutic interventions, and allow corrective changes to improve treatment.

In some instances, the therapy module may rely on the diagnostic module in order to classify subjects as having different conditions or different severity levels of a condition. Optionally, the therapy module can have its own independent prediction module or recommendation module in order to decide on next best therapy or treatment from a list of options. This decision can take into account the assessment from the diagnostic module, as well as independently compiled statistics relating to the historical probability for certain patients to respond to certain treatments, broken down by demographics like gender/age/race/etc. The therapy module can perform the predictive task using simple rules or sophisticated machine learning techniques. In the case of machine learning, an independent feedback loop would take place, connecting patient treatment outcome back to the therapy module.

In some instances, a third-party system, such as a computer system of a health care professional, can be connected to the communication network 120. The health care professional or other third party can be alerted to significant deviations from the diagnosis provided by the diagnostic module and/or therapies suggested by the therapy module based on the reduced number of questions. Appropriate further action can then be taken by the third party. For example, third-party system can review and modify therapies suggested by the therapy module.

In some instances, the patient can have response profiles in response to the therapies, and the therapy module can be configured to categorize the response profiles based on an initial response of the subject. For example, the subject could have a response profile that indicates the treatment is working or a response profile indicating that treatment is not working. These initial response profiles can be somewhat counter intuitive. For example, a fluctuation in symptoms could be an indicator that the treatment is working even though these fluctuations could include an increase and a decrease in a symptom relative to baseline. For some treatments, the time at which there's a change in symptoms could be delayed.

The user, such as the patient and caregivers, can for example download and install an App comprising software instructions on the digital device 110. The App can enable the user to receive instructions from the cloud-based server for the diagnostic tests, upload the answers to diagnostic tests, receive a treatment (for example, games or interactive content) from the cloud-based server, offer feedback, periodically receive new tests to determine how the treatment is progressing, and receive updated treatment. The app can be installed on a plurality of digital devices, such as a first device for the subject to receive digital therapy and second device for the caregiver to monitor progress of the therapy. A feedback loop is thus created between the user and the cloud-based server (for example, the personalized medicine system 130), in which the evaluation of the subject subsequent to the initiation of therapy is used to adjust therapy to improve the response.

Experimental Data

A data processing module as described herein was built on Python 2.7, Anaconda Distribution. The training data used to construct and train the assessment model included data generated by the Autism Genetic Resource Exchange (AGRE), which performed in-home assessments to collect ADI-R and ADOS data from parents and children in their homes. ADI-R comprises a parent interview presenting a total of 93 questions, and yields a diagnosis of autism or no autism. ADOS comprises a semi-structured interview of a child that yields a diagnosis of autism, ASD, or no diagnosis, wherein a child is administered one of four possible modules based on language level, each module comprising about 30 questions. The data included clinical diagnoses of the children derived from the assessments; if a single child had discrepant ADI-R versus ADOS diagnoses, a licensed clinical psychologist assigned a consensus diagnosis for the dataset for the child in question. The training data included a total of 3,449 data points, with 3,315 cases (autism or ASD) and 134 controls (non-spectrum). The features evaluated in the training data targeted 3 key domains: language, social communication, and repetitive behaviors.

A boosted Random Forest classifier was used to build the assessment model as described herein. Prior to training the assessment model on the training data, the training data was pre-processed to standardize the data, and re-encode categorical features in a one-hot representation as described herein. Since the training data was skewed towards individuals with autism or ASD, sample weighting was applied to attribute up to 50 times higher significance to data from non-spectrum individuals compared to data from autistic/ASD individuals. The assessment model was trained iteratively with boosting, updating the weighting of data points after each iteration to increase the significance attributed to data points that were misclassified, and retraining with the updated significances.

Figure 14:
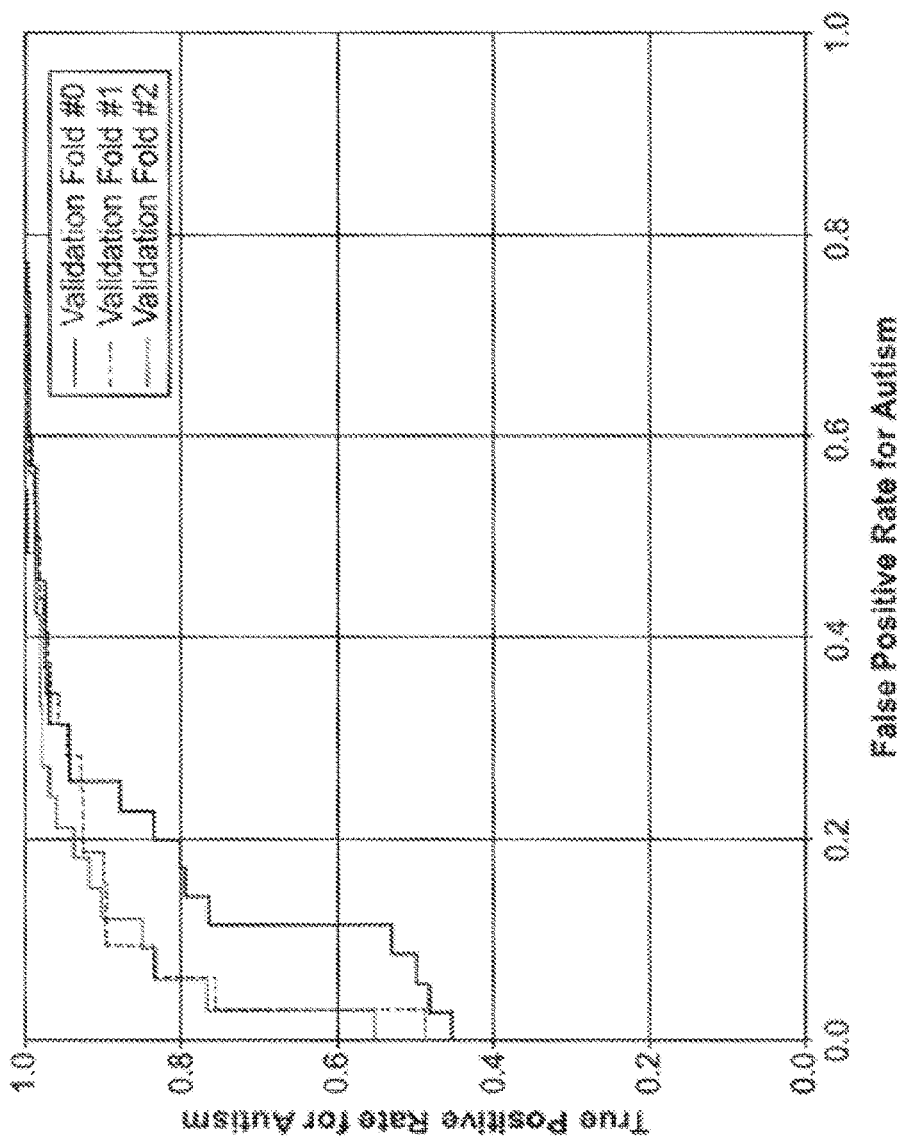
FIG. 14 shows receiver operating characteristic (ROC) curves mapping sensitivity versus fall-out for an exemplary assessment model as described herein.

The trained model was validated using Stratified k-fold cross validation with k=5. The cross-validation yielded an accuracy of about 93-96%, wherein the accuracy is defined as the percentage of subjects correctly classified using the model in a binary classification task (autism/non-spectrum). Since the training data contained a sample bias, a confusion matrix was calculated to determine how often the model confused one class (autism or non-spectrum) with another. The percentage of correctly classified autism individuals was about 95%, while the percentage of correctly classified non-spectrum individuals was about 76%. It should be noted, however, that the model may be adjusted to more closely fit one class versus another, in which case the percentage of correct classifications for each class can change. FIG. 14 shows receiver operating characteristic (ROC) curves mapping sensitivity versus fall-out for an exemplary assessment model as described herein. The true positive rate (sensitivity) for the diagnosis of autism is mapped on the y-axis, as a function of the false positive rate (fall-out) for diagnosis mapped on the x-axis. Each of the three curves, labeled "Fold #0", "Fold #1", and "Fold #2", corresponds to a different "fold" of the cross-validation procedure, wherein for each fold, a portion of the training data was fitted to the assessment model while varying the prediction confidence threshold necessary to classify a dataset as "autistic". As desired or appropriate, the model may be adjusted to increase the sensitivity in exchange for some increase in fall-out, or to decrease the sensitivity in return for a decrease in fall-out, as according to the ROC curves of the model.

Figure 15:
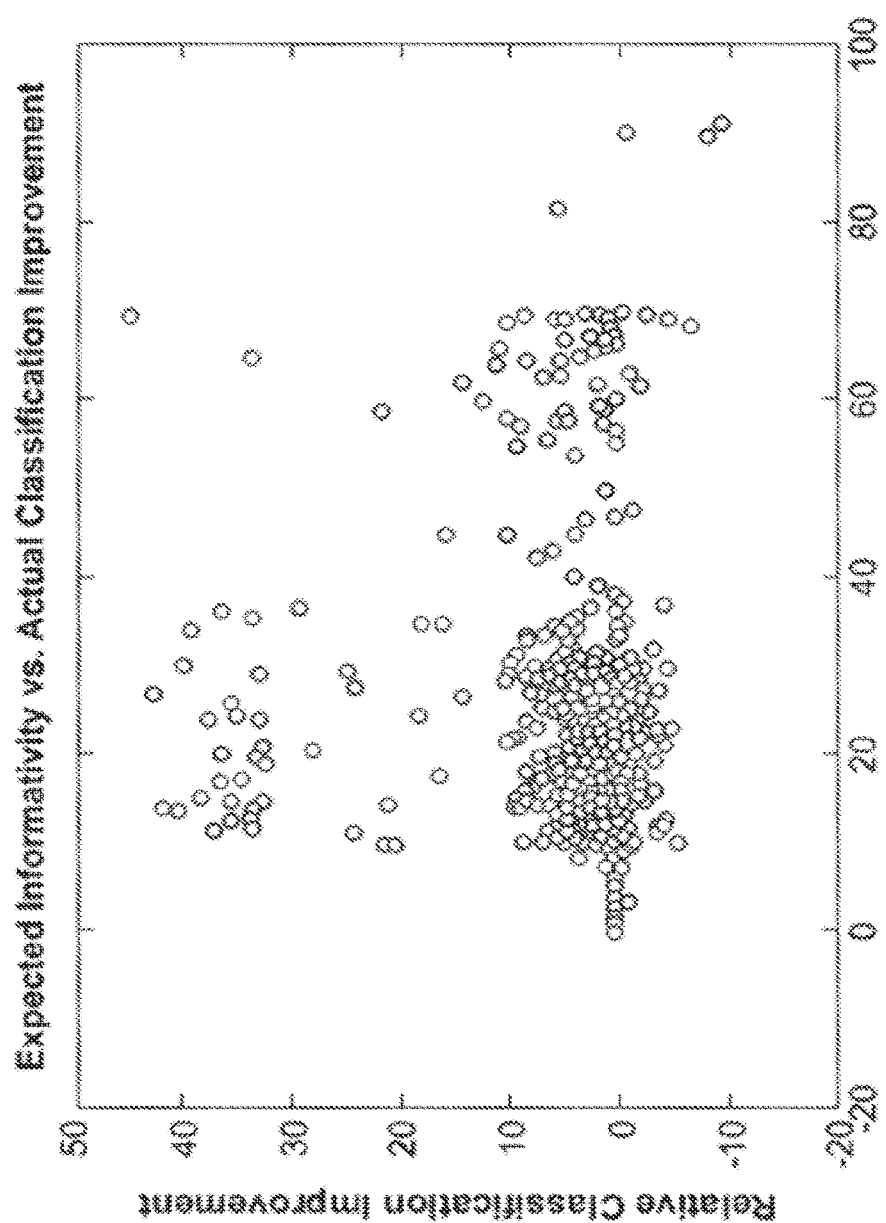
FIG. 15 is a scatter plot illustrating a performance metric for a feature recommendation module as described herein.

The feature recommendation module was configured as described herein, wherein the expected feature importance of each question was computed, and candidate questions ranked in order of computed importance with calls to a server with an application program interface (API). The feature recommendation module's ability to recommend informative questions was evaluated by determining the correlation between a question's recommendation score with the increase in prediction accuracy gained from answering the recommended question. The following steps were performed to compute the correlation metric: (1) the data was split up into folds for cross-validation; (2) already answered questions were randomly removed from the validation set; (3) expected feature importance (question recommendation/score) was generated for each question; (4) one of the questions removed in step 2 was revealed, and the relative improvement in the subsequent prediction accuracy was measured; and (5) the correlation between the relative improvement and the expected feature importance was computed. The calculated Pearson correlation coefficient ranged between 0.2 and 0.3, indicating a moderate degree of correlation between the expected feature importance score and the relative improvement. FIG. 15 is a scatter plot showing the correlation between the expected feature importance ("Expected Informativitiy Score") and the relative improvement ("Relative Classification Improvement") for each question. The plot shows a moderate linear relationship between the two variables, demonstrating the feature recommendation module is indeed able to recommend questions that would increase the prediction accuracy.

The length of time to produce an output using the developed prediction module and the feature recommendation model was measured. The prediction module took about 46 ms to make a prediction of an individual's risk of autism. The feature recommendation module took about 41 ms to generation question recommendations for an individual. Although these measurements were made with calls to a server through an API, the computations can be performed locally, for example.

While the assessment model of the data processing module described with respect to FIGS. 9-10 was constructed and trained to classify subjects as having autism or no autism, a similar approach may be used to build an assessment model that can classify a subject as having one or more of a plurality of behavioral, neurological or mental health disorders, as described herein.

A person of ordinary skill in the art can generate and obtain additional datasets and improve the sensitivity and specificity and confidence interval of the methods and apparatus disclosed herein to obtain improved results without undue experimentation. Although these measurements were performed with example datasets, the methods and apparatus can be configured with additional datasets as described herein and the subject identified as at risk with a confidence interval of 80% in a clinical environment without undue experimentation. The sensitivity and specificity of 80% or more in a clinical environment can be similarly obtained with the teachings provided herein by a person of ordinary skill in the art without undue experimentation, for example with additional datasets.

Additional datasets may be obtained from large archival data repositories as described herein, such as the Autism Genetic Resource Exchange (AGRE), Boston Autism Consortium (AC), Simons Foundation, National Database for Autism Research, and the like. Alternatively or in combination, additional datasets may comprise mathematically simulated data, generated based on archival data using various simulation algorithms. Alternatively or in combination, additional datasets may be obtained via crowd-sourcing, wherein subjects self-administer the assessment procedure as described herein and contribute data from their assessment. In addition to data from the self-administered assessment, subjects may also provide a clinical diagnosis obtained from a qualified clinician, so as to provide a standard of comparison for the assessment procedure.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein. For example, one or more aspects, components or methods of each of the examples as disclosed herein can be combined with others as described herein, and such modifications will be readily apparent to a person of ordinary skill in the art. For each of the methods disclosed herein, a person of ordinary skill in the art will recognize many variations based on the teachings described herein. The steps may be completed in a different order. Steps may be added or deleted. Some of the steps may comprise sub-steps of other steps. Many of the steps may be repeated as often as desired, and the steps of the methods can be combined with each other.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method of evaluating an individual for a behavioral disorder, a neurological condition, or a developmental delay, said method comprising:

providing, with a digital device, digital interactive content to said individual;

obtaining, with said digital device, input data based on interactions of said individual with said digital interactive content, said input data comprising (i) feedback data by said individual in response to said individual interacting with said digital interactive content on said digital device and (ii) video data of a face of said individual captured using a camera of said digital device, wherein said digital interactive content is capable of changing responsive to said feedback data, wherein one or more features are extracted, by said digital device, from said feedback data and used, by said digital device, to select a next feature to be evaluated by dynamically updating said digital interactive content, wherein said next feature includes a most predictive feature for evaluating said individual for said behavioral disorder, said neurological condition, or said developmental delay, wherein eye tracking on one or both eyes of said individual in said video data is used to determine a direction and duration of a gaze of said individual interacting with said digital interactive content, wherein said direction and duration of said gaze corresponds to eye fixation on a screen of said digital device, eye saccades, or both;

evaluating said input data, using an assessment model trained with machine learning, to detect an indication of a presence of said behavioral disorder, said neurological condition, or said developmental delay based at least on said direction and duration of said gaze of said individual interacting with said digital interactive content; and providing said indication of said presence of said behavioral disorder, said neurological condition, or said developmental delay to said individual, a caregiver, or an independent party, wherein said behavioral disorder, said neurological condition, or said developmental delay comprises autism or autism spectrum disorder;

wherein said digital device is a tablet or smartphone comprising a mobile app configured to capture said interactions of said individual with said digital interactive content.

2. The computer-implemented method of claim 1, wherein said assessment model comprises features for evaluating language, social communication, repetitive behaviors, or any combination thereof.

3. The computer-implemented method of claim 1, wherein said input data comprises a heat map of eye focus on said screen of said digital device generated based on said eye tracking.

4. The computer-implemented method of claim 1, wherein said assessment model comprises a neural net.

5. The computer-implemented method of claim 1, wherein obtaining said input data of said individual with said digital interactive content comprises capturing audio of said individual.

6. The computer-implemented method of claim 5, wherein said evaluating said input data comprises analyzing said audio of said individual to evaluate at least one of speech pattern, lexical or syntactic pattern, or higher order linguistic pattern.

7. The computer-implemented method of claim 1, wherein said evaluating said input data comprises analyzing said video of said individual to evaluate facial expression or features.

8. The computer-implemented method of claim 7, wherein analyzing said video of said individual comprises identifying a face or landmarks on the face and determining at least one facial expression.

9. The computer-implemented method of claim 1, wherein said evaluating said input data comprises analyzing said video of said individual to track movement of a hand of said individual.

10. The computer-implemented method of claim 1, further comprising obtaining feedback or updates from said individual and uploading said feedback or updates to a cloud-based server for analysis.

11. The computer-implemented method of claim 1, further comprising providing a test or questionnaire and obtaining additional input data comprising responses to said test or said questionnaire.

12. The computer-implemented method of claim 1, further comprising providing a digital therapeutic for treating said individual for said autism or autism spectrum disorder based at least on said indication of said presence of said behavioral disorder, said neurological condition, or said developmental delay.

* * * * *